US008821859B2

(12) United States Patent
Yang et al.

(10) Patent No.: US 8,821,859 B2
(45) Date of Patent: Sep. 2, 2014

(54) METHODS AND ARTICLES FOR THE DELIVERY OF THERAPEUTIC AGENTS

(75) Inventors: Yi-Yan Yang, Singapore (SG); Yong Wang, Singapore (SG); Cherng-wen Tan, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1276 days.

(21) Appl. No.: 10/849,498

(22) Filed: May 19, 2004

(65) Prior Publication Data
US 2005/0260276 A1 Nov. 24, 2005

(51) Int. Cl.
*A61K 38/43* (2006.01)
*C12N 9/00* (2006.01)
*C12N 5/00* (2006.01)

(52) U.S. Cl.
USPC .......... 424/94.1; 435/183; 435/196; 435/375; 424/94.5

(58) Field of Classification Search
CPC ............ A61K 38/43; C12N 9/00; C12N 9/16; C12N 5/00
USPC ....................................... 424/94.1
See application file for complete search history.

(56) References Cited

U.S. PATENT DOCUMENTS

| 6,696,038 B1* | 2/2004 | Mahato et al. ................ 424/1.45 |
| 2002/0045263 A1* | 4/2002 | Leong et al. ................... 435/455 |
| 2002/0131951 A1 | 9/2002 | Langer et al. |
| 2003/0129223 A1 | 7/2003 | Wartchow et al. |
| 2003/0134420 A1* | 7/2003 | Lollo et al. ..................... 435/455 |
| 2003/0211165 A1 | 11/2003 | Vogel et al. |

FOREIGN PATENT DOCUMENTS

| WO | WO98/19710 | * 5/1998 | ............ A61K 47/48 |
| WO | WO 01/72280 | 10/2001 | |
| WO | WO01/91725 | * 12/2001 | ............... A61K 9/00 |
| WO | WO03/094971 | * 11/2003 | ............. A61K 47/18 |

OTHER PUBLICATIONS

Wang et al "Novel Branched Poly(Ethylenimin)-Cholesterol Water-soluble Lipopolymers for Gene Delivery" in Biomacromolecules, published Sep. 7, 2002, vol. 3 p. 1197-1207.*
Pistel et al in "Brush-like branched biodegradable polyesters, part III: Protein release from microsheres of poly(vinyl alcohol)- graft-poly(D,L-lactic-co-glycolic acid)" (Journal of Controlled Release; 2001, vol. 73:pp. 7-20).*
Liggins & Burt in "Polyether-polyester diblock copolymers for the preparation of paclitaxel loaded polymeric micelle formulations" (Advanced Drug Delivery Reviews, 2002, vol. 54, pp. 191-202).*
Cotten, M. et al., "High-Efficiency Receptor-Mediated Delivery of Small and Large (48 kilobase Gene Constructs Using the Endosome-Disruption Activity of Defective or Chemically Inactivated Adenovirus Particles," Proc. Nat'l. Acad. Sci. USA 89:6094 (1992).
Dong, D.C. et al., "The Py Scale of Solvent Polarities," Can. J. Chem. 62:2560 (1984).
Haensler, J. et al., "Polyamidoamine Cascade Polymers Mediate Efficient Transfection of Cells in Culture," Bioconjug. Chem. 4:372 (1993).
Kataoka, K. et al., "Block Copolymer Micelles for Drug Delivery: Design, Characterization and Biological Significance," Adv. Drug Delivery Rev. 47:113 (2001).
Kishida, T. et al., "ElectroChemo-Gene Therapy of Cancer: Intratumoral Delivery of Interleukin-12 Gene and Bleomycin Synergistically Induced Therapeutic Immunity and Suppresses Subcutaneous and Matastatic Melanomas in Mice," Molecular Therapy 8:738 (2003).
Kunath, K. et al., "Low-Molecular-Weight Polyethylenimine as a Non-Viral Vector for DNA Delivery: Comparison of Physicochemical Properties, Transfection Efficiency and in Vivo Distribution With High-Molecular-Weight Polyethylenimine," J. Control. Release 89:113 (2003).
Luo, D. et al., "Synthetic DNA Delivery Systems," Nature Biotechnol. 18:33 (2000).
Malone, R.W. et al., "Dexamethasone Enhancement of Gene Expression After Direct Hepatic DNA Injection," J. Biol. Chem. 269:29903 (1994).
Pack, D.W. et al., "Design of Imidazole-Containing Endosomolytic Biopolymers for Gene Delivery," Biotechnol. & Bioeng. 67:217 (2000).
Zauner, W. et al., "Polylysine-Based Transfection Systems Ultilizing Receptor-Mediated Delivery," Adv. Drug Del. Rev. 30:97 (1998).
Zhang, X.H. et al., In Vivo Gene Delivery via Portal Vein and Bile Duct to Individual Lobes of the Rat Liver Using a Polylysine-Based Nonviral DNA Vector in Combination with Chloroquine, Human Gene Therapy 12:2179 (2001).
Invitation to Pay Additional Fees and Search Report dated Mar. 1, 2006 for International Application No. PCT/US2005/017709.

* cited by examiner

*Primary Examiner* — Catherine Hibbert
(74) *Attorney, Agent, or Firm* — Wolf, Greenfield & Sacks, P.C.

(57) ABSTRACT

Articles and methods for the delivery of drugs and/or nucleic acids. Articles including a nanoparticle are provided that may be used for the delivery of a drug, a nucleic acid, or both, to a subject. The articles may be of polymeric material and may self-assemble.

20 Claims, 13 Drawing Sheets

METHODS AND ARTICLES FOR THE DELIVERY OF THERAPEUTIC AGENTS

BACKGROUND OF THE INVENTION

1. Field of the Invention

The invention relates to an article and method for the delivery of nucleic acids or drugs and, in particular, to an article and method for the co-delivery of a nucleic acid and a drug.

2. Discussion of the Related Art

The delivery of DNA to cells is an important aspect of many therapeutic and diagnostic procedures in the fields of medical treatment and research. Methods of delivering DNA to cells are typically divided into viral and non-viral gene delivery systems. In general, viral systems have been more effective at transfecting the DNA to the target cell, while non-viral systems are typically safer and easier to produce. Non-viral delivery methods include liposomal delivery vehicles and peptide-DNA complexes. Also included are mechanical methods, such as microinjection, pressure and particle bombardment. Electrically oriented techniques include electroporation at different voltages. Chemical techniques include the use of DEAE-dextran, calcium phosphate, lipids, proteins, dendrimers and other polymers. (Luo, D. & Saltzman W. M. Synthetic DNA delivery systems. *Nature Biotechnol.* 18, 33-37 (2000).)

Specific polymers include polyethyleneimine (PEI), polylysene (pLys), and polyamidoamine dendrimers. These materials typically work by condensing DNA in aqueous media and then delivering the DNA to a target such as a cell.

Successful transfection of DNA to a cell can involve more than just delivering the DNA to the cell membrane. The DNA must pass through the cell membrane and be delivered, intact, to the nucleus of the cell in order, for example, to succeed in transferring a vector for the purposes of therapy. Furthermore, this transfection preferably should occur without causing death or damage to the cell that is being treated. Gene therapy and other methods that make use of DNA transfection may be more successful when used in conjunction with a drug that can, for example, help to stabilize the DNA, facilitate delivery of the DNA to the nucleus, or stabilize the cell that is being transfected. Different drugs may also be used in conjunction with gene therapy for the treatment of a specific disorder. For example, both gene therapy and chemotherapy may be useful in treating specific forms of cancer.

SUMMARY

The invention provides articles, compounds, compositions and methods useful in the delivery or co-delivery of materials such as drugs and/or nucleic acids.

In one aspect, an article for delivering a drug and a nucleic acid is provided, the article comprising a nanoparticle having a first portion capable of associating a nucleic acid and a second portion capable of associating a drug.

In another aspect, a composition is provided, the composition comprising a chemical having the structure:

$$-(X-Y-Z)_q-(X'-Y'-Z')_p-$$

wherein X, Y and Z, are selected, independently, from $$\overset{O}{\underset{}{\|}}-(CH_2)_n- \quad \overset{R}{\underset{}{|}}N-(CH_2)_m- \quad \text{and/or} \quad \overset{O}{\underset{}{\|}}-O-(CH_2)_p-$$

and
at least one of X', Y' and Z' includes R', and X', Y' and Z' are selected, independently, from $$\overset{R}{\underset{R'}{\overset{|}{N^+}}}-(CH_2)_{m'}- \quad \overset{O}{\underset{}{\|}}-(CH_2)_{n'}- \quad \text{and/or} \quad \overset{O}{\underset{}{\|}}-O-(CH_2)_{p'}-;$$

wherein, R is H, an alkyl or a substituted alkyl,
R' is a hydrophobic group; and
n, m, p, n', m' and p' are greater than zero.

In another aspect, a method of administering a drug and a nucleic acid to a subject is provided, the method comprising providing a drug/nucleic acid complex, the complex including a non-nucleic acid drug molecularly associated with a nucleic acid, and delivering the complex to the subject.

In another aspect, a method of making a drug delivery composition is provided, the method comprising providing a fluid comprising a polymer and a drug, allowing the polymer to form a micelle having an interior and an exterior, the drug being associated with the interior of the micelle, and associating a nucleic acid with the exterior of the micelle.

In another aspect, a kit is provided, the kit comprising a container including an amphoteric polymeric nanoparticle, a drug associated with a first portion of the nanoparticle, a nucleic acid associated with a second portion of the nanoparticle, and instructions for administering the nanoparticle to a subject.

In another aspect, a kit is provided, the kit comprising a container including an amphoteric polymeric powder capable of associating both a nucleic acid and a non-nucleic acid drug and instructions for associating a non-nucleic acid drug and a nucleic acid with the polymeric powder.

In another aspect, a composition of matter is provided, the composition of matter comprising a nanoparticle, a non-nucleic acid drug associated with a first portion of the nanoparticle, and a nucleic acid associated with a second portion of the nanoparticle.

Other advantages, novel features, and objects of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

DETAILED DESCRIPTION

Figure 1:
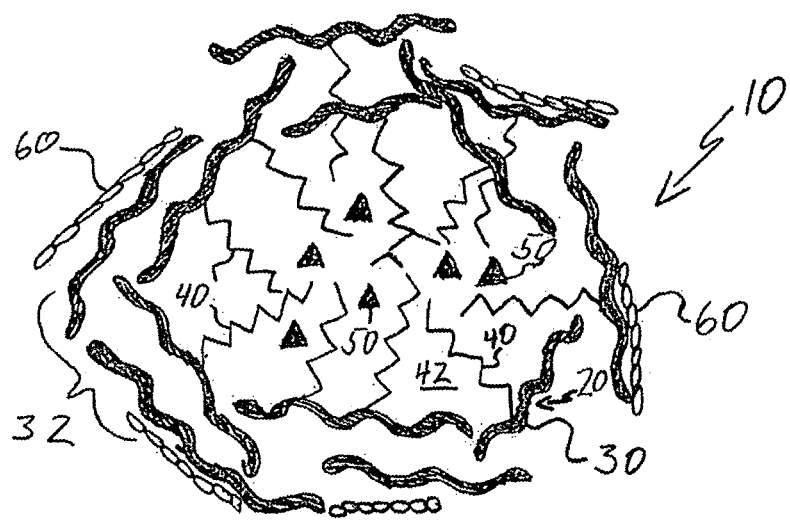
FIG. 1 provides a schematic illustration of a nanoparticle of the invention associated with a drug and a nucleic acid.

The present invention provides articles and methods for the delivery of nucleic acids, non-nucleic acid drugs or a combination of nucleic acids and non-nucleic acid drugs. Both a drug, specifically a non-nucleic acid drug, and a nucleic acid, such as DNA, may be associated with a nanoparticle allowing the drug and nucleic acid to be concurrently delivered to a cell. The articles and methods may be useful, for example, for delivering DNA to a subject, e.g., a mammal, for gene transfection such as may be desired during gene therapy and with other therapeutic techniques. A drug may be delivered to the cell with the nucleic acid allowing for additional therapies or for improving the effectiveness for the desired transfection.

The articles of the invention may have lower cytotoxicity compared to conventionally-used gene carriers under comparative conditions. However, experimental data show that the nanoparticle/DNA complexes yield at least an equivalent level of in vitro gene expression when compared with conventional techniques. In addition, successful gene expression has been achieved using core-shell nanoparticles of the invention. A variety of compounds can be co-delivered with plasmid DNA to enhance gene transfection or achieve a synergy of drug and gene therapies. For example, such a system may be used to carry an anti-cancer drug, such as paclitaxol, or cisplatin, in its hydrophobic core, while binding a nucleic acid agent to its hydrophilic corona. The nucleic acid component may be a vector that encodes an antisense molecule directed against the P-glycoprotein mRNA in the target cell. It is believed that this will inhibit P-glycoprotein expression by the target and incapacitate its ability to effect multi-drug resistance, a common trait among cancer cells. This, coupled with the cytotoxic effects of the anti-cancer drug, and other advantages, may improve the therapeutic effect of gene delivery.

In connection with the present invention, a "nanoparticle" is a particle that can be suspended in a fluid and has a maximum cross-sectional dimension of no more than 1 μm. Nanoparticles can be made of material that is, e.g., inorganic or organic, polymeric, ceramic, semiconductor, metallic (e.g. gold), non-metallic, crystalline, amorphous, or a combination. Typically, nanoparticles used in accordance with the invention are of less than 250 nm cross section in any dimension, more typically less than 100 nm cross section in any dimension, and in most cases are of about 2-30 nm cross section. One class of nanoparticles suitable for use in the invention is 10-30 nm in cross section, and another about 2-10 nm in cross section. As used herein this term includes the definition commonly used in the field of biochemistry.

A "micelle" is a chemical structure that is present in or is formed in an aqueous solution and includes a hydrophilic region in contact with the aqueous solvent and a hydrophobic region that is oriented away from the aqueous solvent. Typically, a micelle is a generally spherical shape with a hydrophobic core and a hydrophilic surface.

"Zeta potential" provides a measurement of the affinity of one particle for another. Zeta potential measures the difference in the electrical charge between a layer surrounding a particle and the charge of the bulk of the suspended fluid that surrounds the particle. Zeta potential is typically measured in millivolts.

"Critical association constant" (CAC) provides a concentration at which a collection of molecules will self-assemble into an ordered structure.

A first molecule may be "associated" with a second molecule, under set conditions, if the two molecules move together as a unit under these conditions. For example, the two molecules may be immobilized with respect to each other. The two molecules may be covalently or ionically bonded, may be joined by Van der Waal's forces or magnetic forces or one molecule may be physically contained or trapped by the second molecule or a collection of second molecules.

A first molecule may be "disassociated" from a second molecule or article with which it is associated. Disassociated means that the first molecule can move independently of the second molecule. The first molecule can also be disassociated from a second molecule or from an article if the second molecule or article degrades or is broken down so that it is no longer linked to the first molecule.

An "amphoteric" polymer is a polymer that exhibits both hydrophilic and hydrophobic properties.

"Physiological conditions" are those chemical conditions that exist in vivo. Such conditions may include temperature, pressure, pH, ionic strength, etc.

In one aspect, a core-shell nanoparticle may associate with both a drug, such as a non-nucleic acid drug, and a nucleic acid. In an embodiment illustrated in FIG. 1, a core shell nanoparticle for the delivery of a drug, a nucleic acid, or both may be made from a grafted polymer. Polymeric compound 20 may include a backbone 30 and a grafted section 40 having different properties than does the backbone 30. For example, the backbone may include polar functional groups to provide polarity to the backbone while the branch 40 may include a hydrophobic group. Hydrophobic groups may include, for example, cholesterol, PLA, PLGA and polyphenols. In the embodiment shown, a number of polymeric molecules 20 have self assembled to form a generally spherical core shell nanoparticle. The hydrophilic backbone 30 is concentrated at the exterior of the shell and the hydrophobic branches 40 extend inwardly to the interior of the core shell nanoparticle. Selection of components of molecule 20 such that self assembly in this manner takes place is described below. The hydrophilic backbones 30 may orient in a direction that is substantially parallel to the surface of the core shell nanoparticle while the hydrophobic branches 40 may be directed inwardly, generally normal to the exterior shell of the core shell nanoparticle. Core-shell nanoparticles can be formed using techniques such as membrane dialysis and sonication, and may self-assemble under some circumstances.

In one aspect, a nanoparticle is provided that is capable of associating with both a drug and a nucleic acid and is capable of co-delivering the drug and the nucleic acid to a target cell. Referring again to FIG. 1, as shown, the core-shell nanoparticle may have an exterior surface 32 and an interior region 42. A chemical species, such as drug 50, represented by dark triangles in FIG. 1, may be associated with at least one of interior region 42 and exterior surface 32 or a portion of interior region 42 or exterior surface 32. Drug 50 may be a non-nucleic acid drug. A second chemical species, for example, a nucleic acid such as DNA, may be associated with at least a portion of surface 32 or interior region 42. Typically, the nucleic acid will be associated with a region or surface that is not one which is associated with the drug.

As shown in FIG. 1, drug 50 is associated with interior region 42 which is also populated by hydrophobic grafted sections, branches 40 of polymer 20. A nucleic acid 60, such as DNA fragments, is associated with exterior surface 32 of nanoparticle 10, and, specifically, with the charged backbone 30 of polymer 20. Nucleic acids typically carry a negative charge and backbone 30 may carry a positive charge to help associate the nucleic acid 60 to the shell of the core-shell nanoparticle. The drug and nucleic acid need not be covalently or ionically bound to the nanoparticle, but in some cases, covalent or ionic bonds can be used. A chemical species may be associated with the interior of a core-shell nanoparticle through Van der Waals forces or other forces of attraction, or may simply be contained in the core of the nanoparticle. The core-shell nanoparticle may be formed in a manner that results with the drug occupying a portion of the core. There may be no diffusion path or other mechanism for the drug to become unassociated with the interior of the core-shell nanoparticle without the disassociation of the nanoparticle itself.

The core-shell nanoparticle may be biodegradable, allowing a chemical species contained in the core to be disassociated, and released in vivo as the core degrades. The nanoparticle can be tailored to degrade at different rates and under different conditions by varying the composition of the nanoparticle.

Figure 2:
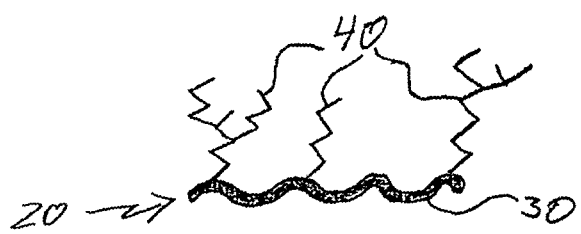
FIG. 2 provides a schematic illustration of a polymeric molecule that may be used to make the nanoparticle of FIG. 1.

FIG. 2 provides a schematic illustration of a compound (which can be a polymer) that can be used to produce a core shell nanoparticle. The polymeric compound 20 includes a backbone 30 that may be hydrophilic and positively charged in order to facilitate associating a nucleic acid. The compound may also include branches or grafts 40 that may be selected to associate a drug. E.g., they may be of a more hydrophobic nature. For example, these branches may include cholesterol or other groups that can be used to associate a non-nucleic acid drug that has a more hydrophobic character. In some embodiments, the polymeric compound of FIG. 2 may be placed in solution with a drug to produce a core shell nanoparticle as shown in FIG. 1. After production of the core shell nanoparticle, the nucleic acid, such as DNA molecule 60, may be associated with the exterior surface of the core shell nanoparticle.

In one aspect, an article of the invention is capable of associating both a nucleic acid and a non-nucleic acid drug with the nanoparticle, or polymeric compound that forms the nanoparticle. In one embodiment, both can be associated simultaneously. The article may form a complex of a drug, a nucleic acid and the article itself. Preferably, the complex can be delivered to a subject, and more specifically, to a particular tissue type or cell type in the subject.

The article may be of any shape or size, and is preferably sized to enter cells via endocytosis. Although the articles may be single molecules or two or more molecules working together, in a preferred embodiment, the article is a core shell nanoparticle that includes an exterior surface and an interior space. The core shell nanoparticle may be composed of any materials capable of associating both a drug and a nucleic acid. For example, the core shell nanoparticle may include a first portion that is charged to associate nucleic acid molecules, such as DNA. A second portion of the core shell nanoparticle may include a hydrophobic region that is capable of associating a non-nucleic acid drug. Thus, the core shell nanoparticle may be used to deliver both a drug and a nucleic acid simultaneously to a target, such as a specific tissue or cell.

In one embodiment, the core shell nanoparticle is sized so that it is suspendible in aqueous solution. Preferably, the core shell nanoparticle is suspendible in an aqueous solution under physiological conditions. The core shell nanoparticles may also be sized so they are capable of penetrating a cell membrane while they are associated with both a nucleic acid and a drug. In this manner, simultaneous delivery of a drug and a nucleic acid to a cell or tissue may be realized. To enter the cell via endocytosis, it is preferred that the nanoparticle be smaller than the cell which it is entering. For example, an article of the invention may be less than about 20 µm in diameter and preferably less than about 5 µm in diameter. In some embodiments, the article is a core shell nanoparticle having a mean diameter of less than 1 µm, less than 500 nm, less than 250 nm, less than 100 nm, or less than 50 nm. The core shell nanoparticle may also have a mean diameter of greater than 10 nm, greater than 20 nm, greater than 50 nm, greater than 100 nm, or greater than 250 nm.

In some embodiments, the core shell nanoparticle is of a generally spherical structure. The spherical structure may include an outer surface and an inner core which may be used to contain a drug. Alternatively, the inner core may be used to contain a nucleic acid while the outer surface may be used to associate a drug.

Many non-viral vectors currently used or proposed for gene therapy exhibit a level of cytotoxicity that makes them less than ideal for treatment of a subject. In one embodiment, the present invention provides for a core shell nanoparticle exhibiting a cytotoxicity lower than that of many known non-viral delivery vectors. For example, the core shell nanoparticle is believed to have a cytotoxicity that is less than that of polyethyleneimine (PEI) or lipofectamine. The IC50 for core-shell nanoparticles may be greater than 160 mg/L, greater than 250 mg/L or greater than or equal to about 500 mg/L. Thus, the core shell nanoparticle may be capable of delivering a drug, a nucleic acid, or both to a cell without injuring or killing the cell due to the presence of the delivery vehicle.

Materials for forming core-shell nanoparticles may also be chosen based on the target that is to be treated. For example, materials may be chosen to release nucleic acid or drug under localized conditions of, for example, pH, temperature, or enzyme concentration. For treatment of the central nervous system, materials capable of crossing the blood brain barrier may be preferred.

After a drug and/or nucleic acid has become associated with a nanoparticle, it is desirable, in some embodiments, to disassociate the drug and/or nucleic acid from the nanoparticle. When both a drug and a nucleic acid are associated with a nanoparticle, the drug and nucleic acid may be disassociated from the nanoparticle simultaneously or at different times. Often, the drug and/or nucleic acid may disassociate from the nanoparticle under physiological conditions. Disassociating may include the breaking of covalent or ionic bonds to release the drug or nucleic acid. Disassociating can also include diffusion of a drug or nucleic acid away from the nanoparticle. Factors such as ionic strength, pH or electrical state may also be varied to facilitate disassociation. Additional compounds may also be administered to a subject or directly to a cell or tissue to promote the disassociation of the drug or nucleic acid.

In another embodiment, the article of the present invention can be disassociated from a drug or nucleic acid via biodegradation. A biodegradable core shell nanoparticle may facilitate the release of a nucleic acid, a drug, or both when positioned to act on a target, such as a cell nucleus. If a drug is associated with the interior core of a nanoparticle, biodegradation of the nanoparticle may allow the drug contained in the nanoparticle to be exposed to the cytoplasm of a cell after the nanoparticle has entered the cell. Likewise, degradation of the nanoparticle may facilitate the release of DNA or other nucleic acid, so that the nucleic acid can be transfected into a target nucleus. The polymer may be chosen so that it is degraded by enzymes that are present in a subject or a targeted region of a subject. For example, polymer degradation may be caused by hydrolysis and may be accelerated by enzymes that are present in plasma. Of course, if the drug can be released from the nanoparticle by diffusion or other means, biodegradability may not be required. The biodegradability of a core shell nanoparticle can be tailored for a specific application. For example, the chemical composition of a polymer-based nanoparticle can be adjusted to allow the nanoparticle to reach its target prior to biodegradation. Preferably, biodegradation does not occur until the nanoparticle has reached its target and does take place after the nanoparticle has reached its target. In other embodiments, nanoparticles of different biodegradabilities may be used together in order to deliver drug or nucleic acid to a target at different times or over an extended time period.

Compositions for nanoparticle manufacture may be chosen by the drug and/or nucleic acid for which they are designed to associate with. A screening test may be performed by one of ordinary skill in the art to determine if a particular composition is capable of associating a drug and/or nucleic acid.

To screen for drug compatibility, the nanoparticle may first be formed, in the presence of the drug, using the techniques described herein (membrane dialysis or dissolution or sonication) or by using other methods known to those skilled in the art. To determine if the drug has been associated with the nanoparticle, any nanoparticles may first be separated from the solution that may contain any free drug that has not been associated with the nanoparticle. This separation may be done, for example, by a liquid/liquid extraction based on the contrasting polarities of the nanoparticle and the drug, by ultrafiltration based on the size of the nanoparticles, or by analyzing the solution for free drug using an immunoassay or other antibody-based test. Once separated from any nanoparticles, the remaining solution can be analyzed, quantitatively, for the presence of the drug. If the amount detected is statistically significantly different from the amount added to the solution, then the drug has been successfully associated with the nanoparticle and the nanoparticle and the drug are a match.

One screening technique for determining if a nanoparticle can be associated with a nucleic acid such as DNA or siRNA is to measure the zeta potential of the nanoparticle. If the zeta potential of the nanoparticle is greater than about +20 mV, then the nanoparticle is appropriate for associating the nucleic acid. Zeta potential can be measured using a zeta potential analyzer with dynamic light scattering capability, such as the ZETAPLUS, available from Brookhaven, USA.

In one embodiment, the core shell nanoparticle may be made from a polymeric compound. The polymeric compound may include a portion capable of associating a nucleic acid and a second portion capable of associating a drug. The polymeric compound may be a branched polymeric compound and the branches may be grafted onto a backbone. In one embodiment, the polymeric compound may be an amphiphilic co-polymer and, more specifically, a cationic amphiphilic co-polymer. The polymeric backbone may include a series of tertiary amines, at least some of which may be quaternized. For example, the backbone may include poly (n-methyldietheneimine sebacate) (PMDS). To obtain a cationic amphiphilic co-polymer, a hydrophilic group, for example, cholesterol, may be grafted onto the polymeric backbone. For instance n-(2-bromoethyl)carbarmoyl cholesterol can be grafted onto PMDS through a quaternization reaction. The amount of grafting can be controlled and targeted to achieve core shell nanoparticles that are capable of delivering a drug and a nucleic acid of predetermined choice. The amount of quaternization of the tertiary amine on the backbone may vary from greater than 1% to less than 100% and may be, for example, greater than 10, greater than 20, greater than 30, greater than 40, greater than 50, greater than 60, or greater than 70%. In other embodiments, the amount of quaternization may be less than 100, less than 90, less than 80, less than 70, less than 60, less than 50, less than 40, less than 30, less than 20, or less than 10%. In one example, a backbone is quaternized to a level of about 39.6% with a hydrophobic cholesterol graft.

The backbone of the polymer may be hydrophilic and may include various functional groups that provide charged or polar regions that can be used to associate nucleic acid such as DNA. For example, the backbone may include an ester linkage, polyester groups, or polyethers. In one embodiment, the polymeric material may be represented by one or more of the co-polymeric structures shown below:

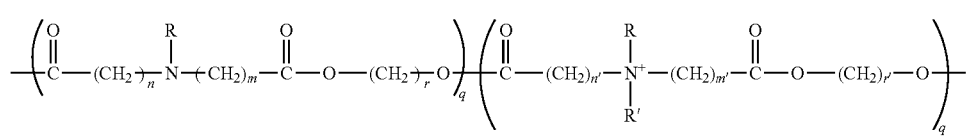

Formula 1 m, n, r, m', n', r'>0
R: H or alkyl group or its derivatives
R': hydrophobic group (e.g. cholesterol, PLA, PLGA and polyphenols etc)

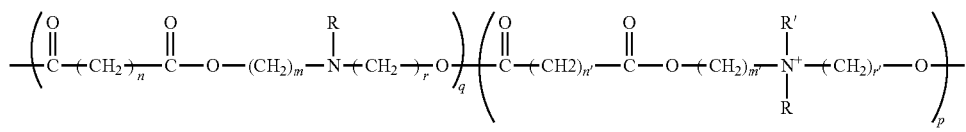

Formula 2 m, n, r, m', n', r'>0
R: H or alkyl group or its derivatives
R': hydrophobic group (e.g. cholesterol, PLA, PLGA and polyphenols etc)

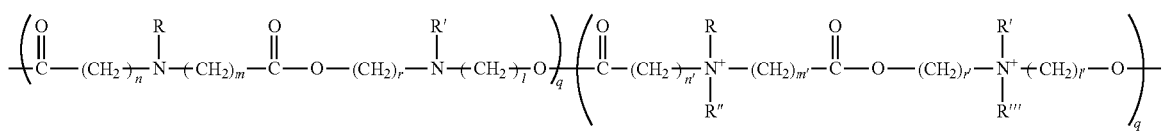

Formula 3 m, n, r, l, m', n', r', l'>0
R, R': H or alkyl group or its derivatives
R'', R''': hydrophobic group (e.g. cholesterol, PLA, PLGA and polyphenols etc)

To tailor the polymer for stability and biodegradability, other compounds may also be grafted into the polymer. These additives can include, for example, one or more of hydrophobically modified PEI, chitosan, and PAMAM dedrimers.

The graft co-polymer may be of any molecular weight (average molecular weight) that results in an article that can associate a nucleic acid and a non-nucleic acid drug. Preferably, the molecular weight of the polymer is within a range that can result in the polymer self-assembling into core-shell nanoparticles under certain conditions. In some embodiments, the molecular weight of the polymers is >1 kDa and less than 50 kDa. Other ranges include from 5 to 50 kDa, from 5 to 30 kDa, from 5 to 20 kDa and from 5 to 15 kDa. In one embodiment, the molecular weight range is between 8 and 12 kDa.

In some embodiments, the compound may be pegylated by grafting a polyethylene glycol group to a portion of the polymer, eg, the backbone. A pegylated polymer may be of particular use, for example, for systemic and/or targeted delivery. Adding one or more PEG groups to a polymer can alter some properties of the polymer, such as solubility, stability, biodegradability and the ability of the compound to enter cells. Examples of pegylated polymers of the invention include pegylated PMDS, pegylated P(MDS-co-CES) and pegylated P(MDA-co-CEA). These can include, for example, poly(ethylene glycol) (Mw 550) (PEG550)-PMDS-PEG550, PEG550-P(MDS-co-CES)-PEG550, PEG 1100-PMDS-PEG 1100, PEG 1100-P(MDS-co-CES)-PEG 1100, PEG2000-PMDS-PEG2000, PEG2000-P(MDS-co-CES)-PEG2000, PEG5000-PMDS-PEG5000, PEG5000-P(MDS-co-CES)-PEG5000, PEG5000-PMDA-PEG5000 and PEG5000-P(MDA-co-CEA)-PEG5000. These compounds can be synthesized using the methods described herein for synthesis of PMDS and P(MDS-co-CES). PEG can be linked to the PMDS or PMDA main chain by using methyl oxide poly (ethyl glycol) as the terminating agent for a condensation reaction when the PMDS or PMDA are synthesized. PEG5000 can be linked to carboxyl acid terminated PMDS and PMDA by using methoxide PEG-hydrazide.

To produce poly{(N-methyldietheneamine adipate)-co-[(chloesteryl oxocarbonylamido ethyl) methyl bis(ethylene) ammonium bromide]adipate}[P(MDA-co-CEA)], adipate $ClC=O(CH_2)_4C=OCl$ can be used in the synthesis instead of the $ClC=O(CH_2)_8C=OCl$ that is typically used in the synthesis of P(MDS-co-CES).

In another embodiment, the polymer can be conjugated to specific molecules that can recognize certain types of cells, for example, cancer cells. For instance, it is known to attach a biomolecule to a nanoparticle so that the nanoparticle can attach to a particular cell. This is called active targeting. (See, eg, Yingjuan Lu and Philip S. Low, "Folate-mediated delivery of macromolecular anticancer therapeutic agents," *Advanced Drug Delivery Reviews,* 54 (2002) 675-693, incorporated by reference herein) In one embodiment of the invention, folate can be attached to a core-shell nanoparticle directly or by a spacer (e.g. PEG) so that the core-shell nanoparticle can recognize cancer cells on the surface of which the folate receptor has been overexpressed. Folate and other groups can be attached to the molecules of the invention by using methods known to those skilled in the art and by the methods described herein. Folate can also be conjugated to the ends of the main chain.

Zeta potential provides a measurement of the repulsion or attraction between particles. For a carrier/DNA complex to be taken up by a cell, it is believed that the zeta potential of the complex should be greater than about 20 mV. Preferably, the articles of the present invention have a positive zeta potential and in some embodiments, the zeta potential may be greater than 20, greater than 40, greater than 60, or greater than 80 mV. In some embodiments, the zeta potential is positive after association with a drug and/or association with a nucleic acid. Therefore, the zeta potential may be positive for a complex that includes a nucleic acid, a drug, and a core shell nanoparticle. A positive zeta potential may facilitate transportation of the drug and the nucleic acid into a cell. In some cases, the inclusion of a drug in the core interior of the core shell nanoparticle may alter the zeta potential of the particle, for example, by raising or lowering it. However, it is often preferred that the zeta potential remain greater than 0 after a drug has been incorporated into the particle.

The articles described herein may be manufactured using techniques known to those skilled in the art. For example, core shell nanoparticles of the invention may be made by dissolution, dialysis membrane techniques, or by an oil and water single emulsion method.

In some embodiments, the core shell nanoparticles can be formed through self-assembly. Using a membrane dialysis method, a core shell nanoparticle may be self-assembled from a polymeric material such as P(MDS-co-CES). The polymer may first be dissolved in a solvent such as a dipolar aprotic solvent, for example, dimethylformamide (DMF), and can then be dialyzed against dionized water or a sodium acetate/acetic acid buffer having a pH of from 4.6 to 5.6. Using this technique, core shell nanoparticles of various sizes can be produced. For example, core shell nanoparticles produced by this method may have effective diameters of about 82, about 96, or about 160 nm. These same nanoparticles may possess polydispersity indices of 0, 0.15, or 0.24.

The core shell nanoparticles of the invention may also be produced directly by dissolving or dispersing the polymer in water and sonicating the dispersion. Experimental results show that the zeta potential may be slightly higher for particles produced by the membrane dialysis method than those produced by the dissolution/sonication method. Therefore, the membrane dialysis method may be preferred to the dissolution/sonication technique.

In another example, the core shell nanoparticle may be produced using an oil in water single emulsion method. The polymer, and any drug that it is to be associated with, can be dissolved in an organic solvent such as DMSO, DMAc, DMF, THF, or DCM. This solution then may be dispersed into an aqueous solvent and the organic solvent can be removed, for example, by extraction or evaporation. The nanoparticles may then be concentrated by, for example, centrifugation.

One measure of how stable a core shell nanoparticle may be in aqueous solution is to measure the critical association concentration (CAC) of the nanoparticle. Typically, the lower the CAC, the more stable the particles will be at lower concentrations. This may be most appreciated in applications where nucleic acid/drug complexes are to be administered to a patient at low concentrations, for example, at less than 100, less than 10, or less than 2 mg/l. The CAC indicates at what concentration the polymeric molecules will self-assemble into a core shell nanoparticle. Polymers that are water soluble, such as PEI, pLys and PAMAM do not exhibit a CAC because they are water soluble. CAC is most applicable to amphiphilic polymers such as pLys-g-PLGA which has a CAC of about 9.6 mg/l and p(MDS-co-CES) having a CAC of about 1.9 mg/l. The CAC of a nanoparticle may be altered by the presence of a drug that is associated with the nanoparticle and therefore it may be advantageous to determine CAC when the polymer is in the presence of a drug that is to be delivered using the resulting nanoparticle.

After production, the core shell particles of the invention may be isolated and dried to form a powder. The powder may then be reconstituted in aqueous solution and/or a pharmaceutically acceptable carrier to facilitate administration to a subject.

A core shell nanoparticle may be a polymeric micelle that includes a positively charged outer surface and a hydrophobic interior core. The outer surface of the nanoparticle may be of any thickness and may be less than 50%, less than 30%, less than 20%, less than 10%, or less than 5% of the diameter of the nanoparticle. Likewise, any hydrophobic grafts that are oriented toward the core of the nanoparticle may completely fill the core or may partially fill the core of the nanoparticle. For example, the hydrophobic grafts may account for less than 100, less than 50, less than 40, less than 30, less than 20, less than 10, or less than 5% of the available volume of the interior of the core shell nanoparticle. Any drugs or nucleic acids associated with the interior of the core shell nanoparticle may be molecularly associated with the hydrophobic grafts or may simply be contained by the enclosed nanoparticle.

In some embodiments, the articles of the invention may be used to treat a subject. For example, a subject may be treated with a complex that includes a nanoparticle, a nucleic acid such as DNA, and a drug. Such treatments may include, for example, gene therapy. A subject may be any mammal that could benefit from treatment with such a complex. For example, the subject may be a human exhibiting symptoms of, or be predisposed to, a particular disorder that may be treated through the use of gene therapy. Such disorders include, for example, genetic disorders as well as cancer and related diseases. It is believed that the following disorders, for which gene therapy has been approved, are among those for which the invention can provide effective treatment.

These disorders include: AIDS, asymptomatic patients infected with HIV-1, HIV infection, HIV infection (identical twins), brain infection, brain tumors, including glioblastoma, recurrent glioblastoma, recurrent pediatric brain tumors, cancer, including advanced cancer, advanced CNS malignancy, advanced renal cell carcinoma, metastatic renal cell carcinoma, breast cancer, (chemo-protection during therapy and post-chemotherapy), metastatic breast cancer (refractory or recurrent), colon carcinoma, advanced colorectal carcinoma, metastatic colorectal cancer, melanoma, including advanced (stage 1V melanoma, disseminated malignant melanoma, malignant melanoma, metastatic melanoma, metastatic prostate carcinoma, ovarian cancer, recurrent pediatric malignant astrocytmas, non-small cell lung cancer, small-cell lung cancer, cystic fibrosis (adults with mild disease), emphysema, familial hypercholesterolemia, Fanconi's anemia, Gaucher's disease, leptomeningeal carcinomatosis, advanced mesothelioma, metastatic melanoma, mild Hunter syndrome (mucopolysaccharidosis type II), pediatric neuroblastoma, relapsed/refractory neuroblastoma, peripheral artery disease, rheumatoid arthritis, and severe combined immune deficiency (SCID) due to adenosine deaminase (ADA) deficiency.

It is also believed that codelivery of nucleic acid (eg, gene) and drug can be beneficial in the case of neurodegenerative diseases such as, for example, Alzheimer's, ALS and Parkinson's. For example, in the case of Parkinson's disease, a treatment can include the co-delivery of the gene for Glial-derived neurotropic factor with a non-nucleic acid drug such as, for example, amantadine hydrochloride. It is believed that amantadine hydrochloride can facilitate dopamine-producing nerve cells to open a "window" and release stored dopamine into the synapse. Therefore, through co-delivery of drug and nucleic acid, it is believed that dopamine can be produced efficiently by gene therapy and can be made readily available in the synapse by the drug. In another embodiment, it is believed that the effective management of the Parkinson's disease can be achieved through the delivery of the gene to produce dopamine, which will be efficiently used with the co-delivery of the drug selegiline hydrochloride that blocks the chemical breakdown of dopamine in the synapse.

The articles of the invention may be applied directly to the tissue that is to be treated, such as by applying a solution including a nanoparticle associated with DNA and a drug to a particular tissue. The article may also be ingested or injected into the circulatory system and may be delivered orally or by injection, preferably after the polymer is pegylated. The articles may also be administered through the cornea or the skin and such administration may be facilitated by the use of electroporation. The articles of the invention are typically administered in aqueous solution or some other pharmaceutically acceptable carrier. Such preparations may routinely contain salts, buffering agents, preservatives, compatible carriers or other therapeutic ingredients. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Time release coatings or enteric coatings may also be used with pharmaceutical compositions of the invention. Those skilled in the art will know of other suitable carriers, or will be able to ascertain such, using only routine experimentation.

The articles of the present invention may be used to associate a wide variety of drugs. Some of the drugs may be administered together with a nucleic acid in order to facilitate transfection of the nucleic acid into a cell of the subject. Other drugs may be used to treat the same or a different disorder than that which is being treated by the nucleic acid. The drug also may serve to stabilize the cell or otherwise protect the cell before, during and after transfection. Some of the drugs that may be used with the articles of the invention include paclitaxol and cisplatin. Others include, for example, doxorubicin, teniposide, etoposide, daunomycin, methotrexate, mitomycin C, indomethacin, ibuprofen, cyclosporin, biphenyl dimethyl dicarboxylate, triamcinolone acetonide, betamethasone, amphotheracin B, ketoconazole, itranazole, daunorubicin, griseofluvin, foropyrimidine, lidocaine, epirubicin, vincristine, vinblastine, ellipticine, camptothecin, docetaxol, prednisone, dexamethasone, bleomycin, chloroquine (endosome escape agent), imidazole (endosome escape agent), doxycyclin and methyl-prednisone.

The core shell nanoparticle may be made using known techniques that can be tailored to provide for release of drugs under specified conditions. For instance, as described in U.S. Pat. No. 6,482,439, hereby incorporated by reference in its entirety herein, compounds such as chondroitin sulfate, hyaluronic acid, chitosan, or a protein may be incorporated into the core shell nanoparticle to facilitate biodegradation by enzymes that act on these species.

Another aspect of the present invention provides one or more compositions of the invention in kits, including instructions for use of the composition for the treatment or prevention of a disorder. Such a kit may comprise a carrier means being compartmentalized to receive in close confinement one or more container means such as vials, tubes, and the like, each of the container means comprising one of the separate elements to be used in the method. The kit may include one or more compositions of the invention in powder form, suspension form or solution form. Instructions may also be provided for forming core-shell nanoparticles from the compositions. The kit also can include instructions for producing an aqueous suspension of the compositions and for forming complexes with drugs and/or nucleic acids that may be included with the kit or may be supplied by the user. Instructions also may be provided for administering the drug orally, intravenously, parenterally, topically, subcutaneously or directly into the cerebro-spinal fluid via a spinal drip, pump, or implantable delivery device.

The function and advantage of these and other embodiments of the present invention will be more fully understood from the examples below. The following examples are intended to illustrate the benefits of the present invention, but do not exemplify the full scope of the invention.

EXAMPLES

Figure 3:
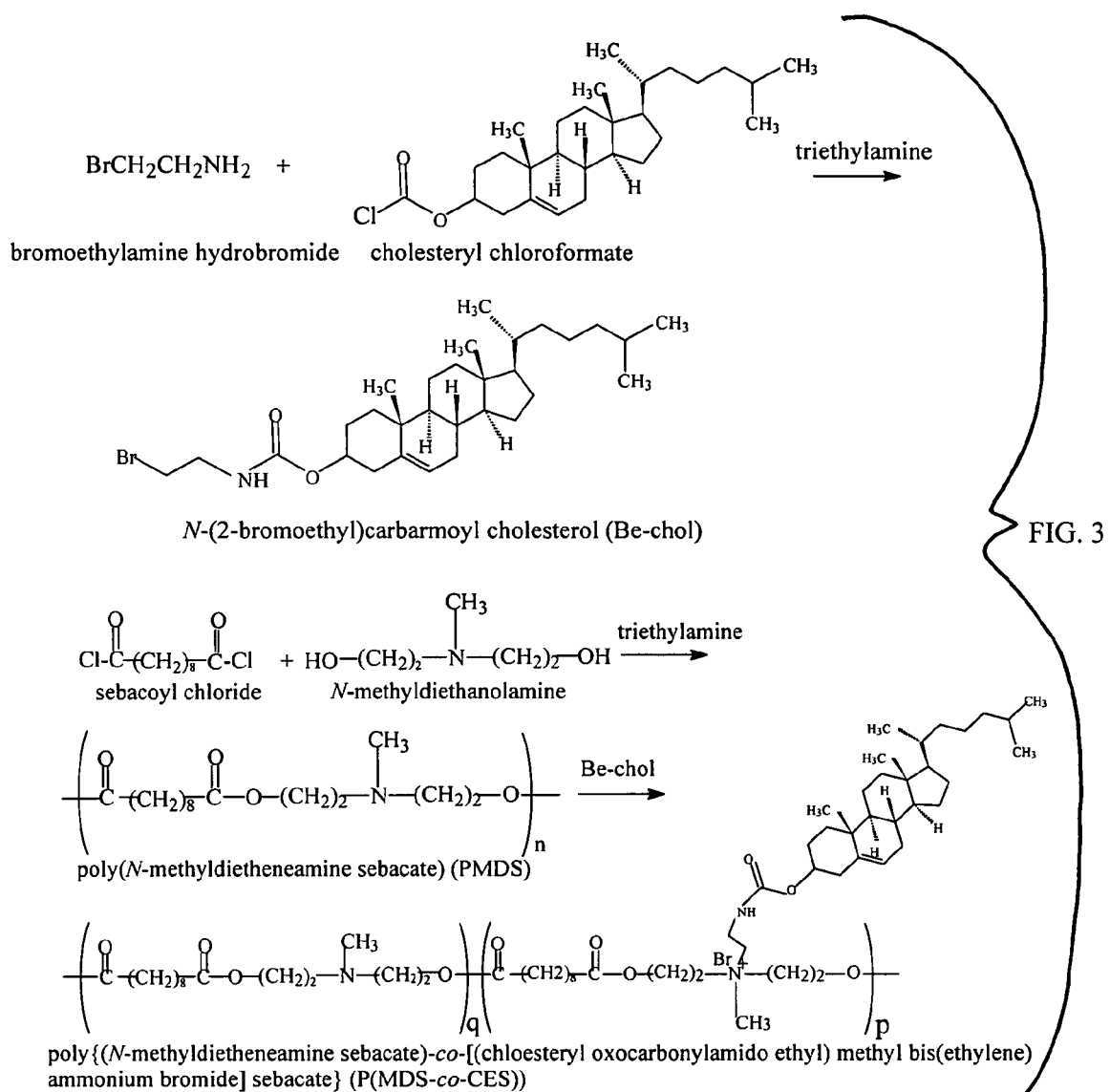
FIG. 3 illustrates a synthetic scheme for manufacturing a compound of the invention.

In one embodiment, a core-shell nanoparticle capable of associating a drug, a nucleic acid, or both may be produced from P(MDS-co-CES). P(MDS-co-CES) was synthesized as described below. A schematic diagram of the synthesis is provided in FIG. 3.

PMDS was produced as follows. 5.958 g N-methyldiethanolamine (0.05 mol) and 50.5 g triethylamine (0.5 mol) were added to a 150 mL of round-bottom flask. While stirring, 40 mL THF (dried with sodium) containing 11.945 g sebacoyl chloride (0.05 mol) was dropped into the flask that was incubated in an ice-water bath. One hour later, the flask was removed and the reaction was allowed to proceed at room temperature for three days. The solvent and residual triethylamine were removed using a rotavapor. The crude product was dissolved in 20 mL chloroform and dialyzed against chloroform using a membrane with a molecular weight cut-off of 3500. Chloroform was removed using the rotavapor and the final product was dried in the vacuum oven for two days. Product yield was about 75%.

N-(2-Bromoethyl) carbarmoyl cholesterol was chosen as the hydrophobic group to be grafted to the polymeric backbone. 50 mL of chloroform dried over molecular sieves was put into 100 mL round-bottom flask, which was incubated in the dry ice/acetone bath at a temperature of less than $-30°$ C. While stirring, 4.34 g cholesteryl chloroformate (0.0097 mol) and 2.18 g 2-bromoethylamine hydrobromide (0.0106 mol) were added. Thereafter, 3 mL freshly dried triethylamine was added to the flask. After half an hour, the flask was taken out and the reaction was allowed to proceed at room temperature for 12 hours. The organic solution was washed three times with 20 mL of 1N HCl aqueous solution saturated with NaCl and once with 30 mL of NaCl-saturated aqueous solution to remove triethylamine. The organic phase was collected and dried with 5 g anhydrous magnesium sulfate. The solution was then filtered and distilled. The crude product was re-crystallized with anhydrous ethanol once and anhydrous acetone twice. The final product was dried with a vacuum oven for 24 hours. Product yield was about 78%.

The N-(2-bromoethyl) carbarmoyl cholesterol was grafted to the PMDS backbone in order to obtain P(MDS-co-CES). 85 g PMDS (0.01 mol) and 5.5 g N-(2-bromoethyl) carbarmoyl cholesterol (0.01 mol) were dissolved in 50 mL dry toluene and refluxed at $120°$ C. for 4 days under argon. The solution was distilled using a rotavapor to remove toluene and 100 mL diethyl ether was then added to precipitate the product. To completely remove unreacted N-(2-bromoethyl) carbarmoyl cholesterol, the product was washed four times with diethyl ether. Product yield was about 70%.

A core-shell nanoparticles of P(MDS-co-CES) was fabricated using a membrane dialysis method. 10.0 mg of P(MDS-co-CES) polymer was dissolved in 5.0 mL dimethylformamide (DMF) and dialyzed against 500 mL deionized water and, in a second run, against sodium acetate/acetic acid buffers with pH values of 4.6 and 5.6. The core-shell nanoparticles had a narrow size distribution and a positive zeta potential as characterized by a zeta potential analyzer with dynamic light scattering capability (ZetaPlus, Brookhaven, USA). Their effective diameters in deionized water, sodium acetate/acetic acid buffers (pH 5.6 and 4.6) were 160, 96 and 82 nm with polydispersity indices of 0.15, 0.24 and 0.24 respectively. The respective zeta potentials of the nanoparticles were 44, 72 and 84 mV. At lower pH, the nanoparticles possessed a higher zeta potential. It is believed that this is due to the protonization of the tertiary amine on the polymer main chain. The resulting core-shell nanoparticles had a slightly higher zeta potential compared to the nanoparticles fabricated by a direct dissolution method. It is believed that this is because the nanoparticles made by the membrane dialysis method have a better organized core-shell structure.

To evaluate the possibility of using this cationic amphiphilic copolymer to co-deliver drug and DNA, model drugs were associated with the core of the core-shell nanoparticles. Indomethacin and pyrene were chosen as model drugs and were encapsulated in the core-shell nanoparticles by the membrane dialysis method. The encapsulation efficiency of indomethacin and pyrene as determined by UV spectroscopy was 78.4% and 55.6% respectively. The particle size increased after drug loading (175 nm vs. 83 nm for indomethacin and 180 nm vs. 83 m for pyrene). However, the zeta potential of the nanoparticles after drug loading decreased (63 mV vs. 84 mV for indomethacin and 65 mV vs. 84 mV for pyrene).

Figure 4:
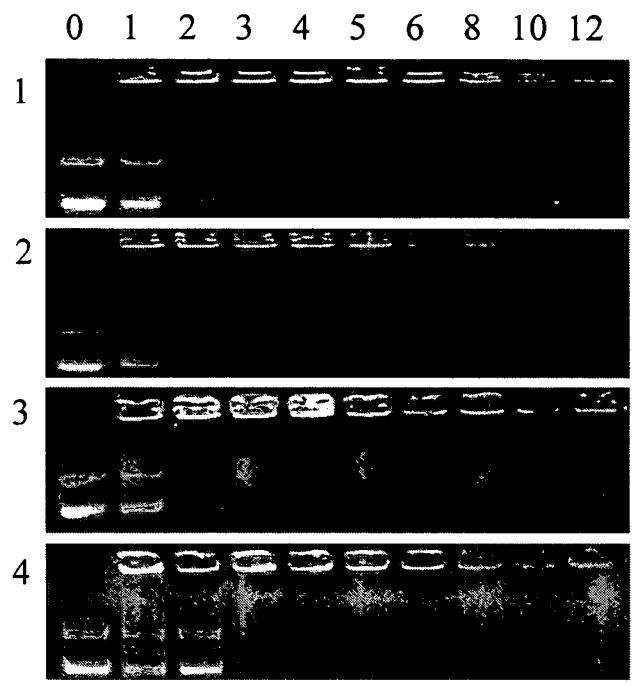
FIG. 4 is a photocopy of an electrophoresis plate showing EMSA results for four different nanoparticles or complexes of the invention.

To determine how well a nucleic acid could be associated with the core-shell nanoparticles, a detectable plasmid DNA was associated with the exterior surface of a P(MDS-co-CES) core-shell nanoparticle. A plasmid DNA encoding the 6.4 kb firefly luciferase (pCMV-luciferase VR1255_C) (Seq ID 1) driven by the cytomegalovirus (CMV) promoter was bound to both free polymer, blank core-shell nanoparticles, and indomethacin or pyrene-loaded core-shell nanoparticles in a sodium acetate/acetic acid buffer (pH 4.6). Plasmid DNA, complexed with the free polymer or core-shell nanoparticles, displayed decreased mobility in an electromobility shift assay (EMSA). FIG. 4 provides results showing data from nanoparticles produced by two different methods and from 2 loaded nanoparticles, each at various N/P ratios from 0:1 to 12:1. The first is a nanoparticle (made by the direct dissolution method)/DNA complex (1), the second is a nanoparticle produced by a different method (made by the membrane dialysis method)/DNA complex (2), the third shows indomethacin-loaded nanoparticles/DNA complexes (3) and the fourth shows pyrene-loaded nanoparticles/DNA complexes (4).

The charge ratio, or N/P ratio, is calculated by comparing the number of nitrogens on the polymer to the number of phosphate groups in the nucleic acid (DNA). For example, a complex having an N/P ratio of 3 would have three times as many nitrogens in the polymer as phosphates in the DNA. Thus, the lower the N/P ratio, the greater the percentage of DNA associated with the complex. Measuring mobility of the DNA, complete retardation of the DNA was achieved at an N/P ratio of 3 for the free polymer, 2 for the blank core-shell nanoparticles, 3 for indomethacin loaded core-shell nanoparticles and 3 for pyrene-loaded core shell nanoparticles. The DNA-binding ability of the blank core-shell nanoparticles was slightly stronger than that of the free polymer, as well as the drug-loaded core-shell nanoparticles, most likely due to their greater zeta potential.

Figure 5:
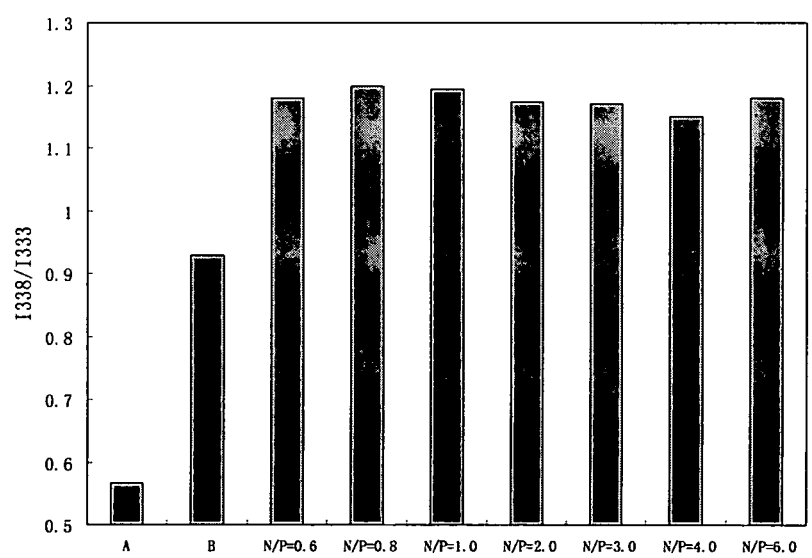
FIG. 5 provides excitation spectra for pyrene, pyrene in core-shell nanoparticles and pyrene in nanoparticle/DNA complexes at various N/P ratios.

In an effort to determine the structural integrity of a drug-loaded core-shell nanoparticle during the DNA binding process, the microenvironment of the loaded pyrene was studied by fluorescence spectroscopy. Fluorescence spectra of pyrene in sodium acetate/acetic acid buffer, pyrene in core-shell nanoparticles in sodium acetate/acetic acid buffer and pyrene in core-shell nanoparticles/DNA complexes at various N/P ratios were obtained on a LS50B luminescence spectrometer (PerkinElmer, USA) at room temperature (22° C.). The intensity (peak height) ratio (1338/1333) of the band at 338 nm to the band at 333 nm from the excitation spectra was analyzed as shown in FIG. 5. A higher ratio was obtained when pyrene was located in a more hydrophobic environment. The ratio 1338/1333 increased with the loading of pyrene into the core-shell nanoparticles. Results show that the binding of DNA further improved the hydrophobicity of the microenvironment of the pyrene, indicating that the pyrene remained in the core of the nanoparticles after DNA binding. It was also found that the size of the pyrene-loaded core-shell nanoparticles/DNA complexes ranged from 150 to 300 nm, with the N/P ratios ranging from 0:1 to 10:1, indicating that pyrene-loaded nanoparticles did not collapse during the DNA binding. These findings demonstrate the ability of these core-shell nanoparticles to carry drug and DNA simultaneously in a stable colloidal solution form.

Figure 6:
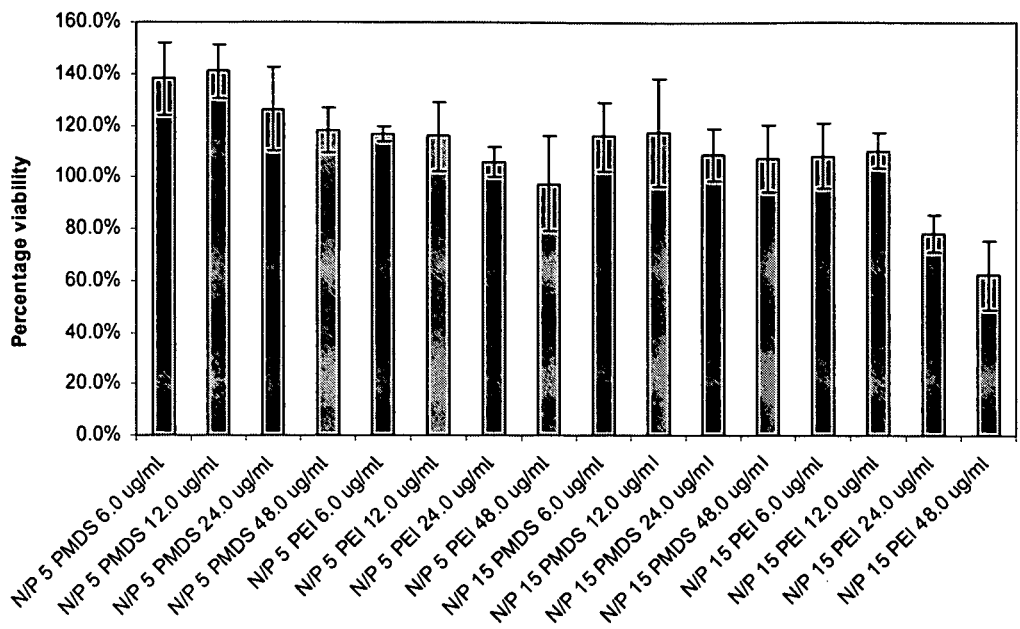
FIG. 6 provides graphic cytotoxicity data at varying N/P ratios.

The cytotoxicity of a core-shell nanoparticle of the invention was evaluated to determine the suitability of the core-shell nanoparticles for in vivo gene delivery. The core-shell nanoparticles/DNA complexes were studied using L929 mouse fibroblasts (ATCC, USA). The L929 fibroblasts were exposed to the core-shell nanoparticles/DNA complexes for three days and did not show any significant cytotoxicity at N/P ratios of 5:1 and 15:1, at concentrations of 6, 12, 24 and 48 µg/mL. In contrast, PEI (branched and Mw=25,000)/DNA complexes at the same N/P ratios displayed cytotoxicity at all four concentrations, this being most pronounced at 48 µg/mL (FIG. 6). Thus, the core-shell nanoparticles described herein provide a safer vehicle for the delivery of nucleic acids that does the PEI/DNA complex.

Figure 7:
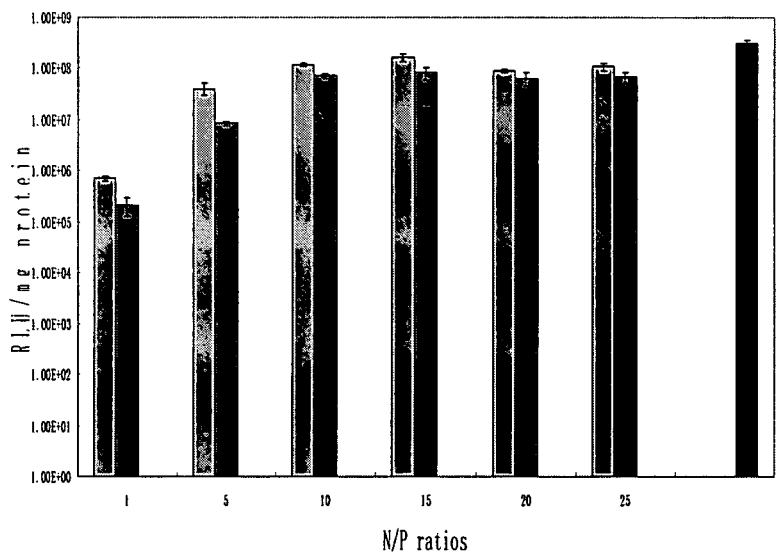
FIG. 7 provides data in bar graph form showing luciferase expression level in cells transfected with the core-shell nanoparticles at various N/P ratios in comparison with PEI.

In another experiment, in vitro transfection experiments were performed on human hepatoma, HepG2 cells and HEK293 cells using the 6.4 kb firefly luciferase reporting gene (pCMV-luciferase VR1255_C) (Seq ID 1) or GFP reporter gene, encoding the GFPmut1 variant (pEGFP-C1) (Seq ID 2) with 4.7 kb driven by the SV 40 early promoter (Clontech, USA) complexed to the core-shell nanoparticles. The nanoparticle/DNA complexes, at different N/P ratios, were incubated with the cells for four hours, at a 2.0 µg DNA dose, in DMEM supplemented with 10% FCS. Results indicate that the transfection efficiency increased with the N/P ratio, reaching maximal transfection efficiency at an N/P ratio of 10:1 (FIG. 7). This transfection efficiency is comparable to that of PEI/DNA complexes in HepG2 cells (black bar). The core-shell nanoparticles made via the membrane dialysis method (lighter bars) provided slightly greater gene transfection efficiency when compared to nanoparticles produced using the solution/sonication method (darker bars).

Figure 8:
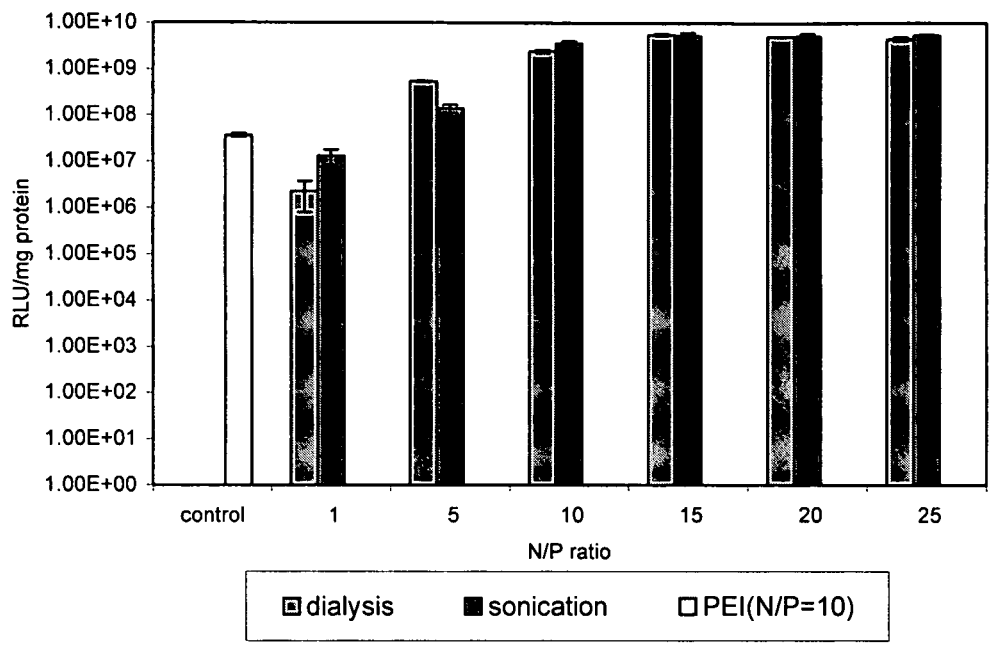
FIG. 8 provides data in bar graph form showing luciferase expression level in HEK 293 cells transfected with the core-shell nanoparticles at various N/P ratios in comparison with PEI.

In HEK293 cells (FIG. 8), the gene transfection reached the highest level at an N/P ratio of 15:1. The nanoparticle/DNA complexes, at different N/P ratios, were incubated with the cells for four hours, at a 2.0 µg DNA dose, in DMEM supplemented with 10% FCS. At an N/P ratio higher than 5:1, the gene transfection level of the nanoparticles/DNA complexes was higher than that of the PEI/DNA complexes. Lighter bars show nanoparticles produced by the membrane dialysis method. Darker bars show nanoparticles produced by sonication. The control (white bar) is PEI at an N/P ratio of 10:1.

Figure 9:
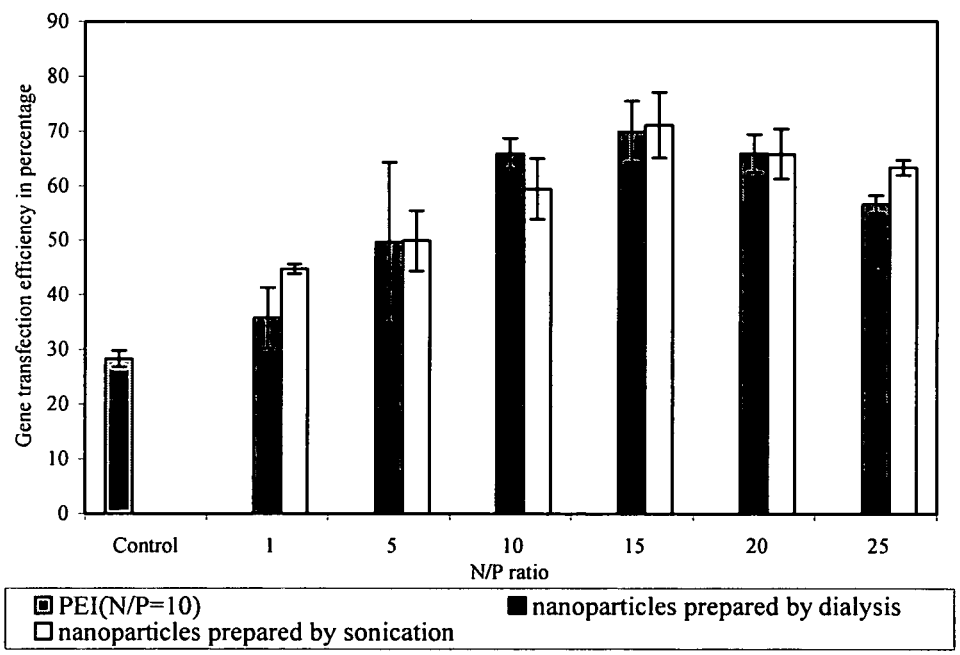
FIG. 9 provides data in bar graph form showing GFP expression efficiency in HEK 293 cells transfected with the core-shell nanoparticles at various N/P ratios in comparison with PEI.

As shown in FIG. 9, GFP expression displayed a similar trend in HEK293 cells. The nanoparticle/DNA complexes, at different N/P ratios, were incubated with the cells for four hours, at a 2.0 µg DNA dose, in DMEM supplemented with 10% FCS. Even at the N/P ratio of 1:1, the number of GFP-positive cells transfected by the nanoparticles/DNA complexes was higher than that transfected by the PEI/DNA complexes.

Figure 10:
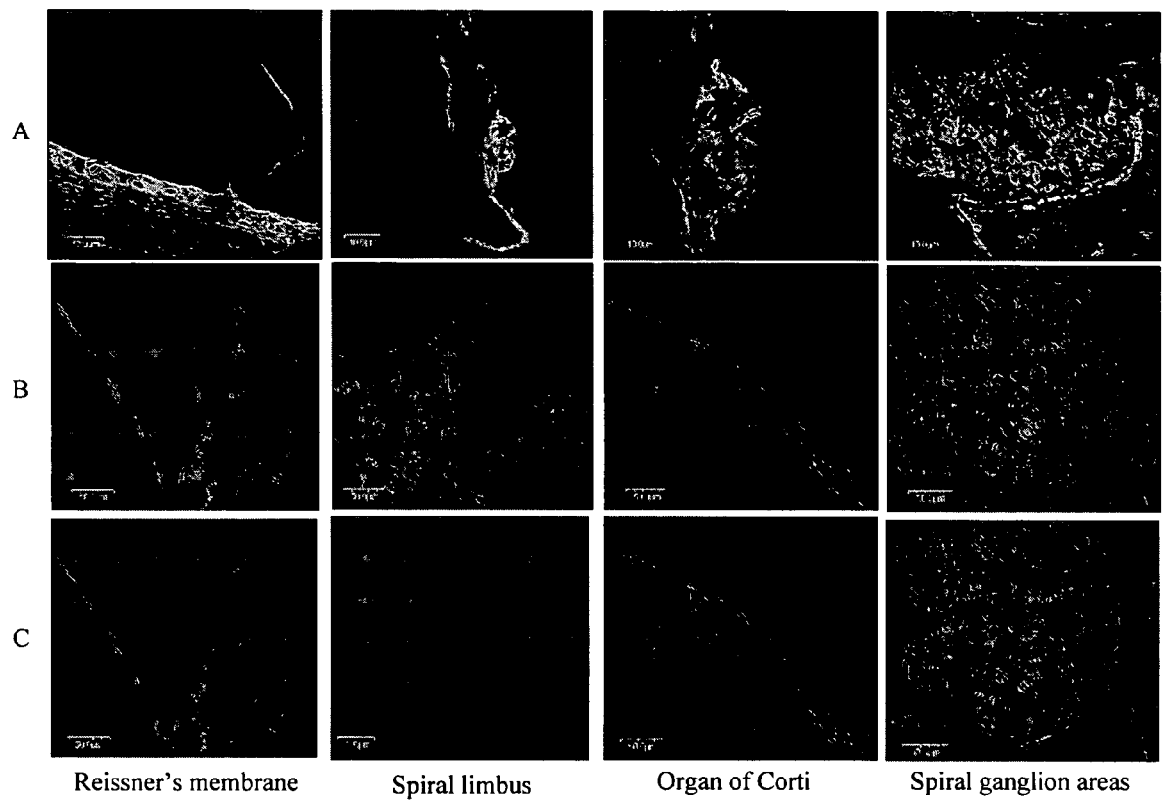
FIG. 10 is a photocopy of a fluorescent micrograph showing enhanced fluorescence in several cochlear tissue types.

In another experiment, in vivo transfection of the cochlea of guinea pigs was completed. GFP reporter gene, encoding the GFPmut1 variant (pEGFP-C1) with 4.7 kb driven by the SV 40 early promoter (Clontech, USA), was employed. The core-shell nanoparticles/DNA complexes with the N/P ratio of 5 were loaded into a piece of gelatin sponge, Gelfoam (Upjohn, Kalamazoo, Mich.). The complex-loaded Gelfoam was placed in contact with the cochlear round window membrane (RWM). Transgene expression of GFPmut1 was observed as fluorescence in nearly all tissue types within the cochlea, including the spiral limbus, Reissner's membrane, the organ of Corti and the spiral ganglion areas. FIG. 10 provides a photocopy of a fluorescent micrograph showing enhanced fluorescence in several cochlear tissue types at Day 7 after administration of a core-shell nanoparticle/GFP-plasmid complex. Lighter areas indicate areas of fluorescence. Row A shows results from the core-shell nanoparticle/DNA complexes; row B shows results for naked DNA, and Row C, at Day 2; the control group.

Figure 11:
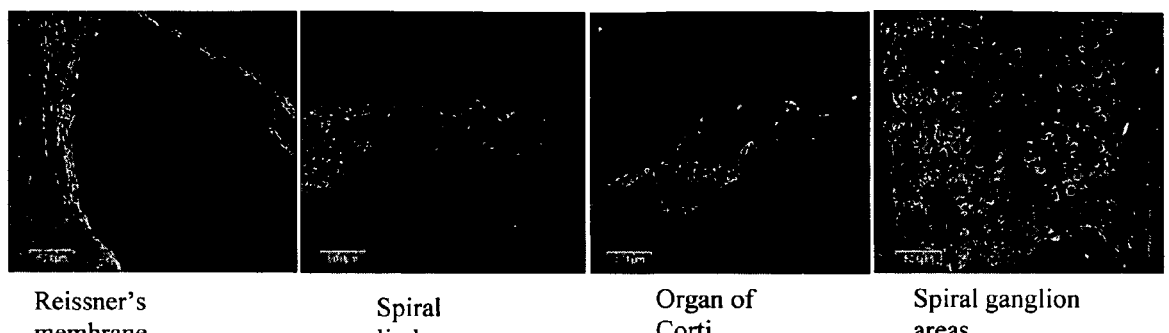
FIG. 11 is a photocopy of a fluorescent micrograph showing similar data to that of FIG. 10 after 14 days.

Sustained transgene expression over 14 days was obtained using the complexes (see FIG. 11). Results show that when the same experiment was run using naked DNA, without the nanoparticle, transgene expression was much weaker. It is believed that these nanoparticles could be used for human cochlear gene therapy in correcting hearing loss.

Synthesis of P(MDS-co-CES)

Synthesis of PMDS: 5.958 g N-methyldiethanolamine (0.05 mol) and 50.5 g triethylamine (0.5 mol) were added to 150 mL of round-bottom flask. With stirring, 40 mL THF (dried with sodium) containing 11.945 g sebacoyl chloride (0.05 mol) was dropped into the flask that was incubated in an ice-water bath. One hour later, the flask was removed out and the reaction was carried out at room temperature for three days. The solvent and residual triethylamine were removed using a rotavapor. The crude product was dissolved in 20 mL chloroform and dialyzed against chloroform using a membrane with a molecular weight cut-off of 3500. Chloroform was removed using the rotavapor and the final product was dried in the vacuum oven for two days. The yield was about 75%.

Synthesis of N-(2-Bromoethyl) carbarmoyl cholesterol: 50 mL of chloroform dried with molecular sieve was put into 100 mL of round-bottom flask, which was incubated in the dry ice/acetone bath (temperature: lower than −30° C.). With stirring, 4.34 g cholesteryl chloroformate (0.0097 mol) and 2.18 g 2-bromoethylamine hydrobromide (0.0106 mol) were added. Thereafter, 3 mL freshly dried triethylamine was added to the flask. After half an hour, the flask was taken out and allowed the reaction to be carried out at room temperature for 12 hours. The organic solution was washed with 20 mL of 1N HCl aqueous solution saturated with NaCl for three times and once with 30 mL of NaCl-saturated aqueous solution to remove triethylamine. The organic phase was collected and dried with 5 g anhydrous magnesium sulfate. The solution was then filtered and distilled. The crude product was re-crystallized with anhydrous ethanol once and anhydrous acetone twice. The final product was dried with a vacuum oven for 24 hours. The yield was about 78%.

Synthesis of P(MDS-co-CES): 2.85 g PMDS (0.01 mol) and 5.5 g N-(2-bromoethyl) carbarmoyl cholesterol (0.01 mol) were dissolved in 50 mL dry toluene and refluxed at 120° C. for 4 days under the argon atmosphere. The solution was distilled using the rotavapor to remove toluene and 100 mL diethyl ether was then added to precipitate the product. To completely remove unreacted N-(2-bromoethyl) carbarmoyl cholesterol, the product was washed with diethyl ether for another four times. The yield was about 70%.

Transfection Studies

HepG2 or HEK293 cells were maintained in Dulbbecco's modified Eagle's medium (DMEM) supplemented with 10% fetal calf serum (FCS) at 37° C. under an atmosphere with 5% $CO_2$. Cells were seeded onto 24-well plates at a density of $8\times10^4$ cells/well (luciferase-plasmid) or 6-well plates at a density of $1\times10^6$ (GFP-plasmid) and cultivated in 0.5 mL DMEM supplemented with 10% FCS. After 24 hours, the culture medium was replaced with fresh medium, and complexes containing 2.0 μg luciferase-plasmid or GFP-plasmid were added to each well. After 4 hours incubation, the culture media were replaced with DMEM containing 10% FCS. After two days, the culture media were removed and the cells were washed with 0.5 mL PBS. Then, 0.2 mL reporter lysis buffer was added to each well to lyse the cells. Thereafter, the cell suspension was subjected to two cycles of freezing and thawing, and was centrifuged at 14,000 rpm for 5 minutes. The relative light units (RLU) were measured using a luminometer (Bio-Rad, USA) and normalized to protein content using the BCA protein assay (Bio-Rad, USA). The GFP-positive cells were counted using a flow cytometer (EPICS ELITE ESP, COULTER, USA). For in vivo experiments, albino guinea pigs weighing between 250 and 300 g were used. Animals were initially anesthetized with a combination of ketamine (40 mg/kg) and the analgesic xylazine (10 mg/kg). Postauricular approach routinely was used for exposure of the tympanic bony bulla. A small opening of the tympanic bulla was carefully made with the use of forceps to yield direct visualization of the round window membrane (RWM). A small piece of dry Gelfoam was placed in the groove, in direct contact with the RWM. An 11.0 μl of complex solution or naked DNA was injected to Gelfoam. Injection of the vector reagent into Gelfoam prevents the spread of solution to neighboring tissues. The incision was closed in layers, and total operating time was approximately 20 minutes. The animals were killed at day 2, 4, 7 and 14 respectively after surgery. Temporal bond were harvested from both sides of the head. Each bulla was opened using rongeurs to expose the cochlea. The stapes was removed and the cochlea was fixed by injection of 4% paraformaldehyde through the round window. The cochlea was then immersed in 4% paraformaldehyde overnight at 4° C. After complete fixation, specimens were decalcified in 10% EDTA for 5 days. After decalcification, the specimens were placed in PBS and dehydrated through a graded alcohol series, and then equilibrated in xylene. The specimens were embedded in paraffin and sectioned radially at a thickness of 7 μm on a Leica microtome (RM2125RT). Tissue sections were dewaxed with xylene and mounted with Sigma mounting medium, and then viewed under a confocal microscope (Olympus, Japan).

1. Synthesis and Characterization of P(MDS-co-CES)

Cholesteryl chloroformate with a purity of 98% was obtained from Aldrich, USA and used as received. N-Methyldiethanolamine with a purity of 99% (Aldrich, USA) was purified with sodium, and then vacuum distilled. Sebacoyl chloride with a purity of 97% (Aldrich, USA) was purified by vacuum distillation. Triethylamine (Sigma, USA) was first treated with toluene sulphonyl chloride to remove secondary amines. It was then distilled and freshly dried with sodium before being used for synthesis. 2-Bromoethylamine hydrobromide with a purity of higher than 99% was obtained from Sigma, USA and used as received. THF (Merck, Germany) was also freshly dried with sodium before use.

1.1 Synthesis and Characterization of Poly(N-methyldietheneamine Sebacate) (PMDS)

5.958 g N-methyldiethanolamine (0.05 mol) and 50.5 g triethylamine (0.5 mol) were in a 150 mL round-bottomed flask and incubated in a dry ice/acetone bath. While stirring, 40 mL of sodium-dried THF containing 11.945 g of sebacoyl chloride (0.05 mol) was added drop-wise into the flask. The flask was removed one hour later and the reaction was allowed to proceed at room temperature for three more days. The solvent and residual triethylamine were removed using a rotavapor. The crude product was dissolved in 20 mL of chloroform and dialyzed against chloroform using a membrane with a molecular weight cut-off of 3500. Chloroform was subsequently removed from the dialysate using the rotavapor and the final product was dried in a vacuum oven for two days. The yield was about 75%.

Figure 12:
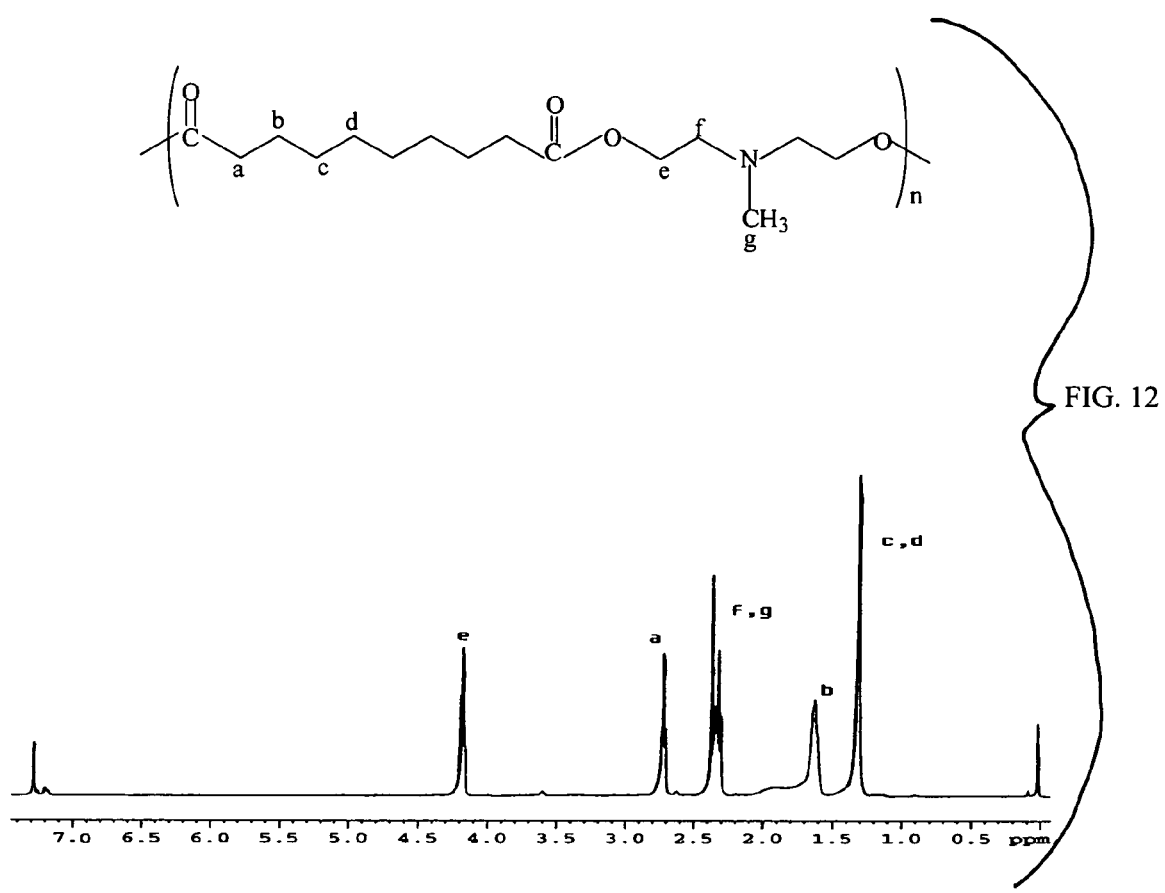
FIG. 12 provides a proton NMR spectrum for PMDS.
Figure 13:
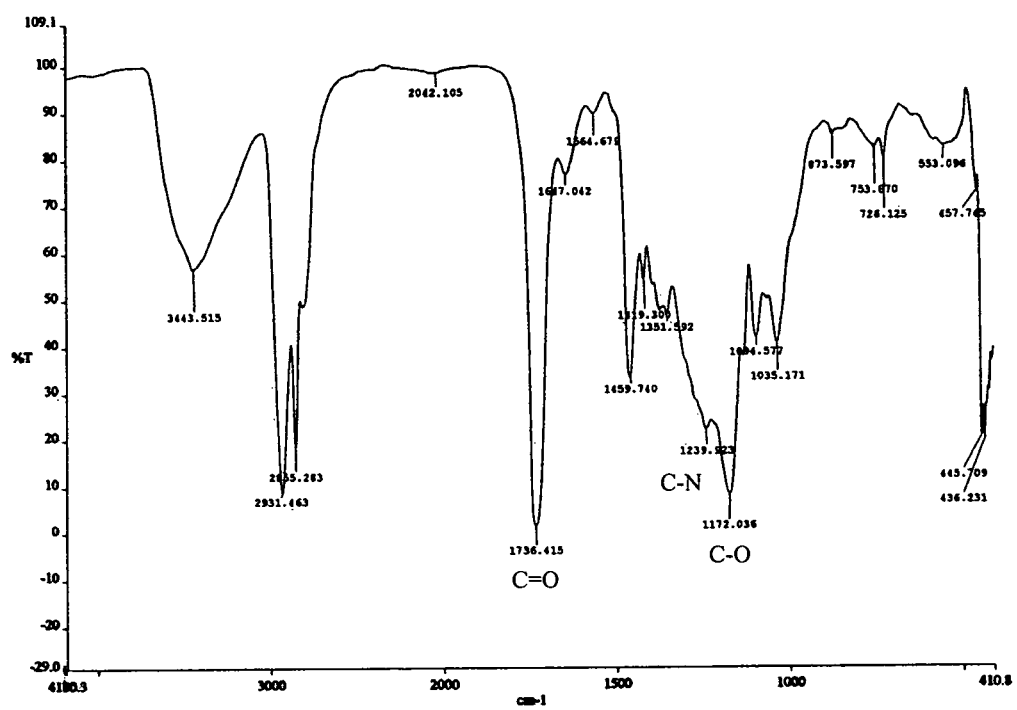
FIG. 13 provides an FTIR spectrum for PMDS.

The structure of PMDS was characterized by $^1$H NMR and FTIR spectra as shown in FIG. 12 and FIG. 13. In FIG. 12, the broad peaks at δ 2.71-2.73 (Signal a), the peaks at δ 1.62 (Signal b) and δ 1.32 (Signals c and d) were attributed to the protons of four different —$CH_2$— groups from the sebacate units. The triple peaks at δ 4.17-4.19 (Signal e) and multiple peaks at δ 2.30-2.37 (Signals f and g) were from the protons of two different —$CH_2$— groups and the —$CH_3$ group linked to the nitrogen atom. The IR spectrum also evidenced the formation of the polyester. As shown in FIG. 13, the stretching vibration of —C═O shifted to the lower wave number (1736 cm$^{-1}$) compared with that of carbonyl halide (1805 cm$^{-1}$) because of the inductive effect of halide. The peak at 1172 cm$^{-1}$ had an intensity comparable to that from the stretching vibration of —C═O, which was attributed to C—O. Both $^1$HNMR and IR studies proved that the synthesis of PMDS was successful.

1.2 Synthesis and Characterization of N-(2-Bromoethyl) carbarmoyl Cholesterol A 100 mL round-bottomed flask containing 50 mL of chloroform dried with a molecular sieve was incubated in a dry ice/acetone bath (temperature: lower than −30° C.). While stirring, 4.34 g of cholesteryl chloroformate (0.0097 mol) and 2.18 g of 2-bromoethylamine hydrobromide (0.0106 mol) were added. Thereafter, 3 mL of freshly dried triethylamine was added to the flask. After half an hour, the flask was taken out and the reaction was allowed to proceed at room temperature for a further 12 hours. The organic solution was washed three times with 20 mL of 1N HCl aqueous solution saturated with NaCl and once with 30 mL of NaCl-saturated aqueous solution to remove residual triethylamine. The organic phase was collected and dried with 5 g of anhydrous magnesium sulfate. The solution was then filtered and distilled. The crude product was re-crystallized with anhydrous ethanol once and anhydrous acetone twice. The final product was dried with a vacuum oven for 24 hours. An analysis by thin layer chromatography (TLC) test showed that its flow ratio ($R_f$) is 0.68 in a solvent mixture of toluene, hexane and methanol (8:8:1 in volume), indicating that the product was pure. The yield was about 78%.

Figure 14:
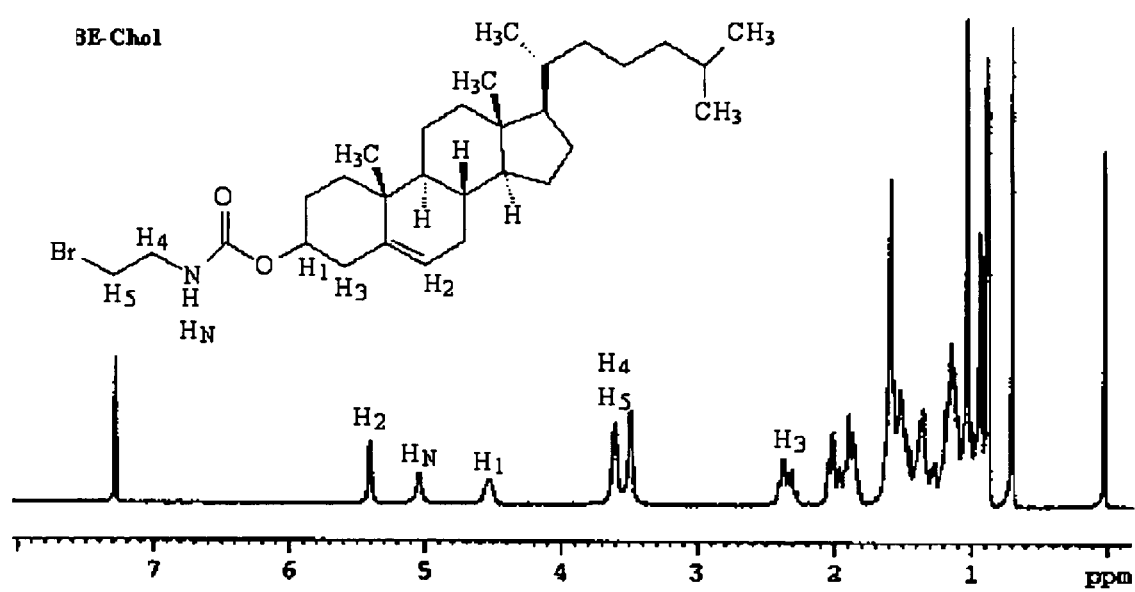
FIG. 14 provides a proton NMR spectrum for N-(2-bromoethyl) carbarmoyl cholesterol.
Figure 15:
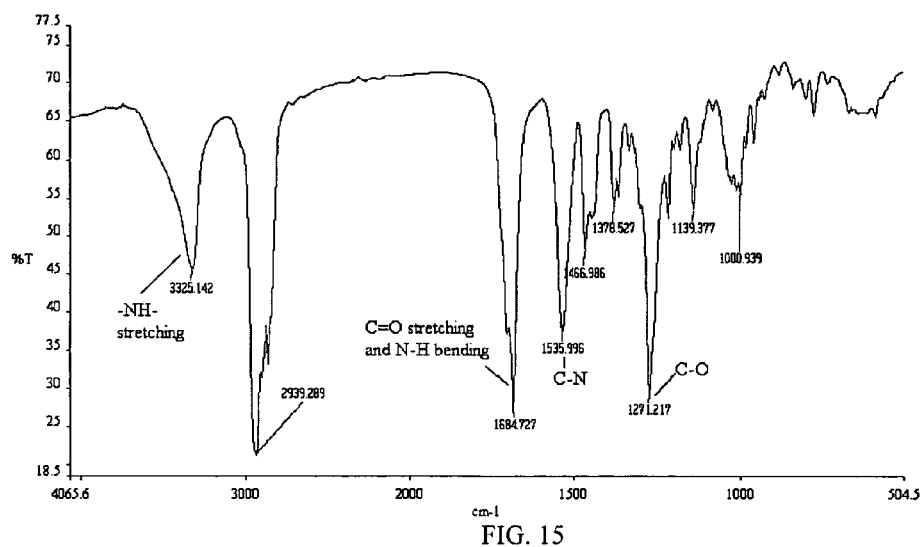
FIG. 15 provides an FTIR spectrum for N-(2-bromoethyl) carbarmoyl cholesterol.

The structure of N-(2-bromoethyl) carbarmoyl cholesterol was characterized by $^1$H NMR and IR spectroscopic methods. As showed in FIG. 14, the proton signal at δ 5.10 (Signal $H_N$) was from amide groups (CONH). The signals from 2-bromoethyl groups are also observed at δ 3.60 (Signal $H_4$) and 3.61 (Signal $H_5$), respectively. The signals at δ 4.52 ($H_1$) and 5.40 ($H_2$) are from the cholesterol units. The integration of the peak areas shows the ratio of $H_1$, $H_2$, $H_N$, $H_4$, and $H_5$ is 1:1:1:2:2, indicating the successful synthesis of N-(2-bromoethyl) carbarmoyl cholesterol. FIG. 15 shows the IR spectrum of N-(2-bromoethyl) carbarmoyl cholesterol. The peak at 3325 cm$^{-1}$ represents the stretching vibration of the —NH— bond. The signals of —C═O stretching and —NH— bending vibration are overlapped at 1685 cm$^{-1}$. The peak at 1536 cm$^{-1}$ is from the stretching vibration of —C—N—. This corroborates the proof of the success of N-(2-bromoethyl) carbarmoyl cholesterol synthesis.

1.3 Synthesis and Characterization of Poly{(N-methyldietheneamine sebacate)-co-[(chloesteryl oxocarbonylamido ethyl) methyl bis(ethylene) ammonium bromide]sebacate} (P(MDS-co-CES))

2.85 g of PMDS (0.01 mol) and 5.5 g of N-(2-bromoethyl) carbarmoyl cholesterol (0.01 mol) were dissolved in 50 mL dry toluene and refluxed at 120° C. for 4 days under an argon atmosphere. The solution was then distilled using the rotavapor to remove the toluene and 100 mL diethyl ether was then added to precipitate the product. To completely remove unreacted N-(2-bromoethyl) carbarmoyl cholesterol, the product was washed with diethyl ether four more times. The yield was about 70%.

Figure 16:
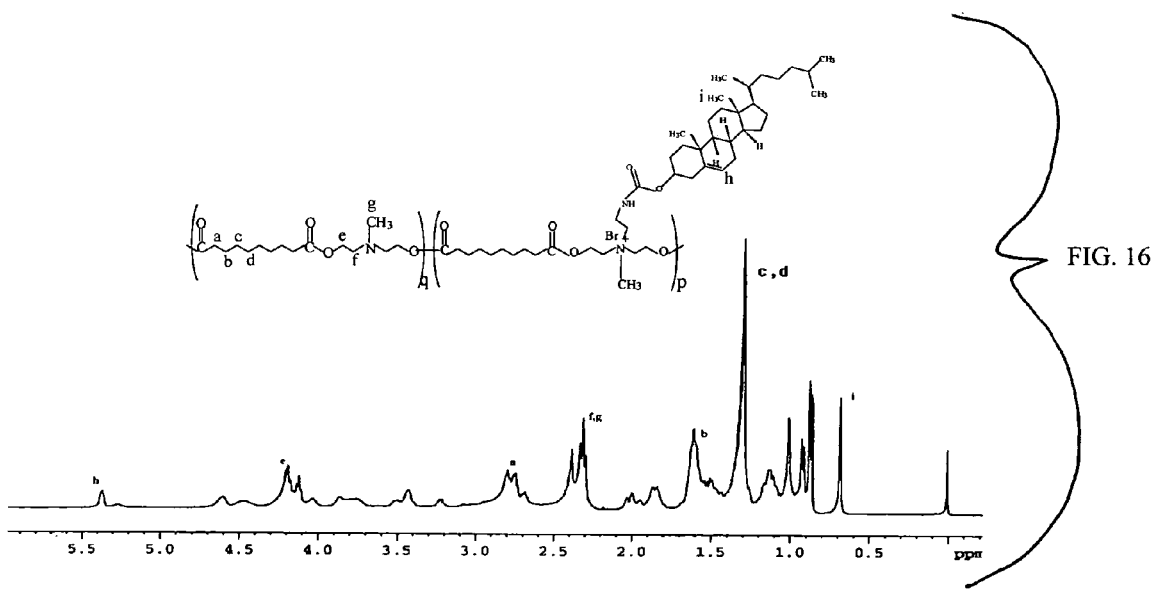
FIG. 16 provides a proton NMR spectrum for P(MDS-co-CES)
Figure 17:
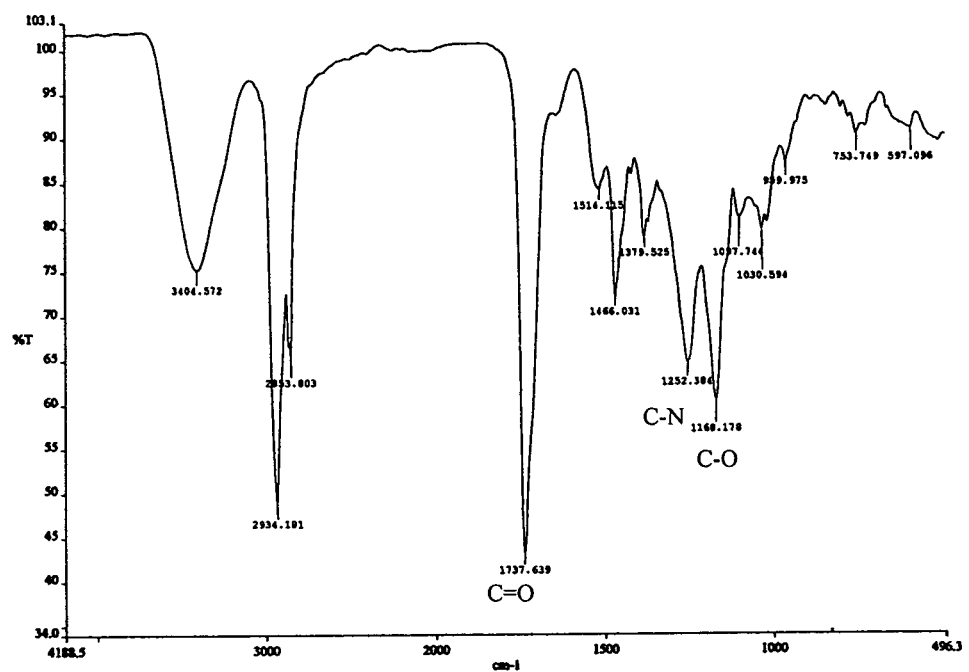
FIG. 17 provides an FTIR spectrum for P(MDS-co-CES)

The $^1$H NMR spectrum of P(MDS-co-CES) is shown in FIG. 16. The peaks at δ 2.7-2.8 (Signal a), 1.5-1.7 (Signal b), 1.2-1.4 (Signals c and d), 4.0-4.2 (Signal e) and 2.2-2.4 (Signals f and g) are from the protons of the PMDS main chain. A number of peaks appearing from δ 0.7 to 1.2 originate from the cholesterol groups. Besides, the peak at δ 5.38 arises from the proton of the double bond carbon (═CH—) in the cholesterol groups (Signal h). The peak at the high magnetic field δ 0.7 represents the methyl group directly linked to the cyclic hydrocarbon (Signal i). The information provided by the $^1$HNMR spectrum of P(MDS-co-CES) indicates that the cholesteryl group has been successfully grafted onto the PMDS main chain. FIG. 17 shows the IR spectrum of P(MDS-co-CES), which also indicates successful quaternization. The peak at 1252 cm$^{-1}$ is due to the C—N stretching vibration of amine. The shift and increased intensity of this peak compared with that in the IR spectrum of PMDS at 1240 cm$^{-1}$ indicates the formation of a quaternary ammonium salt.

The grafting degree can be estimated by calculating the ratio of the peak area in the $^1$HNMR spectrum associated with the hydrogen on the main chain to that of the pendant chain. This is calculated using the following formula, $$Rg=(\Delta A_p N_{Hm}/N_{Hp}\Delta A_m)\times 100\%,$$

where, $R_g$, is the grafting degree, defined to be the ratio of the number of amine quaternized by N-(2-bromoethyl) carbarmoyl cholesterol to the whole number of amine on the PMDS main chain;

$\Delta A_p$, is the area of the selected peak from the pendant chain;

$\Delta A_m$, is the area of the selected peak from the main chain;

$N_{Hp}$, is the number of hydrogen atoms in the selected group from the pendant chain; and, $N_{Hm}$, is the number of hydrogen atoms in the selected group from the main chain.

First of all, suitable protons from the pendant chain and the main chain should be selected; not all the protons can be used to calculate the grafting degree. The proton signal selected should not overlap signals from other protons. Furthermore, those protons influenced by the quaternization of the amine should not be used. The chemical shifts of some protons on the main chain and the pendant chain were influenced by the quaternization of amine. In this synthesis design, only a portion of the amine groups was quaternized. Therefore, the chemical environment of the hydrogen on the methyl or methylene groups directly linked to the quaternary ammonium was very different from that linked to the tertiary amine. Because of the inductive effect of the positive charge of the quaternary ammonium, these protons were deshielded and the chemical shift, δ, of these protons was thus increased. The chemical shift varied depending on the distance between the proton and the quaternary ammonium. As such, the proton signals from the PMDS main chain became complicated after the quaternization of tertiary amine. For instance, the $^1$H NMR spectrum of P(MDS-co-CES) (FIG. 16) showed that some new signals, which were possibly from the protons of the groups directly linked to quaternary ammonium, appeared at δ 4.6-4.7, 4.4-4.5, 3.7-3.9, and 3.2-3.3. Therefore, it is not recommended to choose the protons of the groups linked to the tertiary amine or quaternary ammonium. The proton of the methylene group linked to the carbonyl group (FIG. 16, Signal a) from the main chain and the proton of the methylidyne group (—CH═) linked to the double bond (FIG. 16, Signal h) as well as the proton of the methyl group linked to the hexane and pentane cycles from the pendant chain (FIG. 16, Signal i) were considered suitable for the estimation of grafting degree.

Based on the peak areas of Signal a and Signal h, the grafting degree for P(MDS-co-CES) was estimated to be 39.6%. By changing the molar ratio of the pendant chain to the PMDS main chain, the grafting degree of the cholesterol moiety and the positive charge of resultant P(MDS-co-CES) can be modulated.

The molecular weight of synthesized P(MDS-co-CES) was determined by GPC (Waters 2690, MA, USA) with a Differential Refractometer Detector (Waters 410, Mass., USA). The mobile phase used was THF with a flow rate of 1 mL/min. Weight average molecular weight as well as polydispersity indices were calculated from a calibration curve using a series of polystyrene standards (Polymer Laboratories Inc., MA, USA, with molecular weight ranging from 1300 to 320,000). P(MDS-co-CES) had a weight average molecular weight of 9.1 kDa with a polydispersity of 2.0. The nitrogen content of the polymer was measured to be 4.34% by an elemental analyzer.

2. Determination of Critical Aggregation Concentration (CAC)

Figure 18:
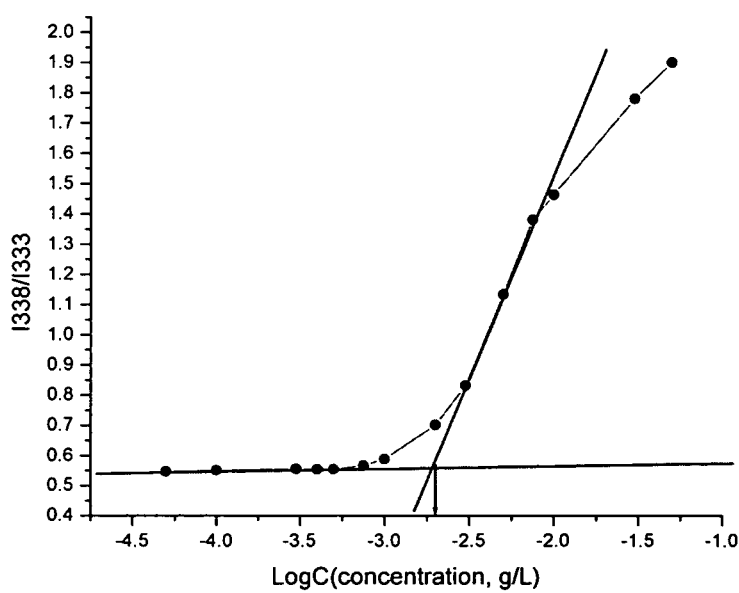
FIG. 18 provides a plot of intensity ratios at varying concentrations.

Aliquots of pyrene solution (10 μg/mL in acetone) were added to 5 mL volumetric flasks, and the acetone was allowed to evaporate. Five millimeters of aqueous polymer solution at concentrations ranging from 0.1 to 50 mg/L were then added to the volumetric flasks containing the pyrene residue. Thus, all the aqueous polymer solutions contained excess pyrene at a concentration of 0.1 μg/mL. The solutions were allowed to equilibrate for 24 hours at room temperature (22° C.). Fluorescence spectra of the polymer solutions were then obtained using a LS50B luminescence spectrometer (Perkin Elmer, USA) at room temperature. The excitation spectra were recorded from 300 to 360 nm with an emission wavelength of 395 nm. The excitation and emission bandwidths were set at 4.5 nm. The intensity (peak height) ratio (I338/I333) of the band at 338 nm to the band at 333 nm from the excitation spectra, was analyzed as a function of polymer concentration. The CAC value (1.9 mg/L) was taken from the intersection of the tangent to the curve at the inflection with the horizontal tangent through the points at the low concentrations as shown in FIG. 18.

3. Preparation of Blank and Drug-Loaded Core-Shell Nanoparticles

The core-shell nanoparticles were fabricated using a membrane dialysis method. P(MDS-co-CES) (10 mg) and indomethacin (2 mg) or pyrene (2 mg) as model drugs were dissolved in 5 mL DMF. The solution was then dialyzed against 1 L deionized water or sodium acetate/acetic acid buffers with pH values of 4.6 and 5.6 using a dialysis membrane with a molecular weight cut-off of 2000 at room temperature for 24 hours. The external phase was replaced hourly for the first 8 hours. The solution was filtered using a filter of 0.45 μm pore size and then analyzed or lyophilized for 24 hours before further examinations were made. The blank core-shell nanoparticles were produced using the same protocol without the addition of model drugs.

4. Transmission Electron Microscope (TEM)

Figure 19:
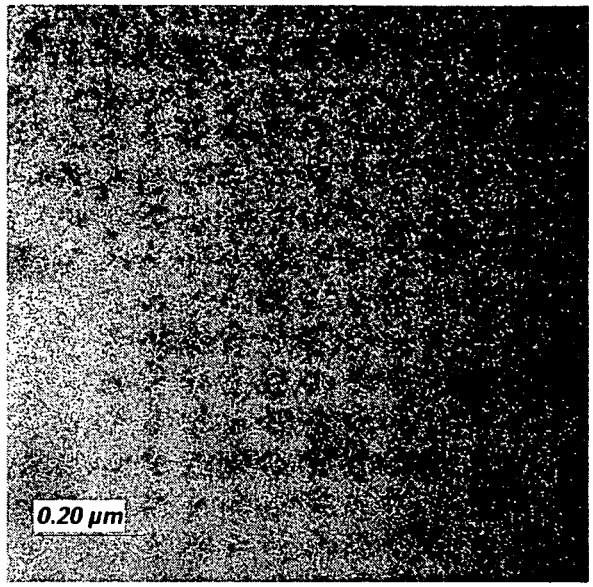
FIG. 19 is a photocopy of a TEM of core-shell nanoparticles of the invention.

A drop of the freshly-prepared nanoparticles solution containing 0.01 (w/v) % phosphotungstic acid was placed on a copper grid coated with carbon film, and was air-dried at room temperature (22° C.). The TEM observations were carried out on a Philips CM300 microscope (Netherlands) with an electron kinetic energy of 300 k eV. FIG. 19 provides a typical TEM image of core-shell nanoparticles fabricated at a polymer concentration of 2 mg/mL.

5. Particle Size and Zeta Potential Measurements

The size, size distribution and zeta potential of blank core-shell nanoparticles, drug-loaded core-shell nanoparticles and drug-loaded core-shell nanoparticles/DNA complexes were measured using a zeta potential analyzer with dynamic light scattering capability (ZetaPlus, Brookhaven, USA). The nanoparticles were freshly prepared as described above. After the mixing of drug-loaded nanoparticles and DNA solution, the complexes were allowed to stand for 30 min prior to the measurements. The size measurements were conducted at a scattering angle of 90°.

Figure 20:
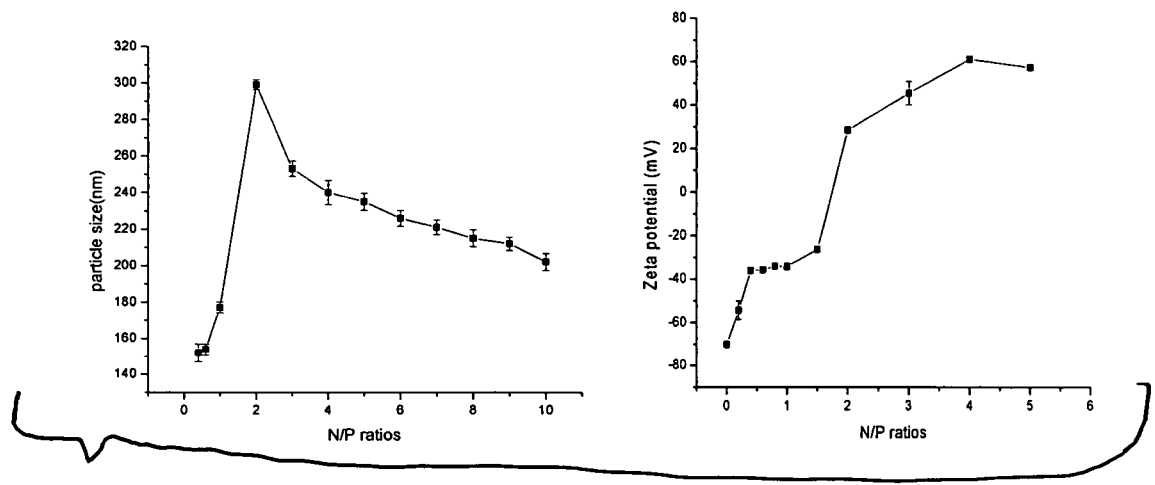
FIG. 20 shows graphically the particle size and the zeta potential of core-shell nanoparticles at varying N/P ratios.

6. Evaluation of Stability of the Drug-Loaded Core-Shell Nanoparticles During the DNA Binding Process FIG. 20 shows the effective diameter and zeta potential of the pyrene-loaded core-shell nanoparticles/DNA complexes as a function of N/P ratio. The pyrene-loaded core-shell nanoparticles were fabricated in the sodium acetate/acetic acid buffer (0.02M, pH 4.6). The nanoparticles were added to the DNA solution (40 μg DNA in 2 mL of the sodium acetate/acetic acid buffer-0.02M, pH 4.6) at various N/P ratios. The size of the pyrene-loaded core-shell nanoparticles/DNA complexes increased with increasing N/P ratio, reaching the maximal size of 300 nm at the N/P ratio of 2. At the N/P ratios ranging from 3:1 to 10:1, the size decreased as a function of N/P ratio. The zeta potential of the complexes reached a constant level at the N/P ratio of 4. During the DNA binding process, the particle size varied within a narrow range (from 150 nm to 300 nm), indicating that pyrene-loaded nanoparticles had not collapsed.

The excitation spectra of pyrene, pyrene-loaded core-shell nanoparticles and pyrene-loaded core-shell nanoparticles/DNA complexes were recorded on an LS50B luminescence spectrometer. Increased I338/I333 ratios of pyrene-loaded core-shell nanoparticles after DNA binding were observed (FIG. 5), indicating that pyrene remained in the core of the nanoparticles and that DNA binding had improved the hydrophobicity of the microenvironment of pyrene. These findings demonstrate the ability of these core-shell nanoparticles to carry drug and DNA simultaneously in a stable colloidal solution form.

7. Drug Loading Level and Encapsulation Efficiency

The loading level and encapsulation efficiency of indomethacin was determined using a UV-VIS spectrometer (Shimadzu UV-2501, Shimadzu, Japan). Briefly, a fixed amount of freeze-dried nanoparticles was dissolved in DMF. The solution was measured directly. The detection wavelength was set at 318 nm for indomethacin and 273 nm for pyrene. The encapsulation efficiency was calculated as the ratio of actual to theoretical drug content.

8. Agarose Gel Electrophoresis

The formation of polymer, core-shell nanoparticles or drug-loaded core-shell nanoparticles/DNA complexes was studied by agarose gel electrophoresis. DNA complexes containing 0.28 μg of luciferase-plasmid at various N/P ratios were loaded into individual wells of 1.0% agarose gel, electrophoresed at 100 V for 90 min, and stained with ethidium bromide. The resultant DNA migration pattern was revealed under UV irradiation.

9. Cytotoxicity Test

The L929 cells were seeded onto 96-well plates at 10,000 cells per well. The plates were then returned to the incubator and the cells were allowed to grow to confluence. On the morning of the initiation of the tests, the media in the wells were replaced with 100 μl of fresh growth medium. Each nanoparticle solution at 50 μl was then added to each well. Phosphate-buffered saline (PBS) at an equivalent volume was used as the negative control. The plates were then returned to the incubators and maintained in 5% $CO_2$, at 37° C., for a period of 24, 48 and 72 hours. Each sample was tested in four replicates per plate. Three plates were used for each period of exposure, making a total of 16 replicates per sample. Aliquots of MTT solution at 20 μl were added into each well after the designated period of exposure. The plates were then returned to the incubator and maintained in 5% $CO_2$, at 37° C., for 3 hours. The growth medium in each well was then removed. 150 μl of DMSO was then added to each well to dissolve the internalized purple formazan crystals. An aliquot of 100 μl was taken from each well and transferred to a fresh 96-well plate. The plates were then assayed at 550 nm and 690 nm using a microplate reader (PowerWave X, Bio-Tek Instruments). The absorbance readings of the formazan crystals were taken to be that at 550 nm subtracted by that at 690 nm. The results were expressed as a percentage of the absorbance of the negative control.

10. In Vitro Transfection Experiments

HepG2 or HEK293 cells were maintained in Dulbbecco's modified Eagle's medium (DMEM) supplemented with 10% fetal calf serum (FCS) at 37° C. under an atmosphere with 5% $CO_2$. Cells were seeded onto 24-well plates at a density of $8 \times 10^4$ cells/well (luciferase-plasmid) or 6-well plates at a density of $1 \times 10^6$ (GFP-plasmid) and cultivated in 0.5 mL DMEM supplemented with 10% FCS. After 24 hours, the culture medium was replaced with fresh medium, and complexes containing 2.0 μg plasmid DNA encoding the 6.4 kb firefly luciferase (pCMV-luciferase VR1255_C) driven by the cytomegalovirus (CMV) promoter/enhancer (luciferase-plasmid) or GFP reporter gene, encoding the GFPmut1 variant (pEGFP-C1) with 4.7 kb driven by the SV 40 early promoter (GFP-plasmid) were added to each well. After 4 hours of incubation, the culture medium was replaced with DMEM containing 10% FCS. After two days, the culture medium was again removed and the cells were washed with 0.5 mL of PBS. Then, 0.2 mL of the reporter lysis buffer was added to each well to lyse the cells. Thereafter, the cell suspension was subjected to two cycles of freezing and thawing, and was centrifuged at 14,000 rpm for 5 minutes. The relative light units (RLU) were measured using a luminometer (Bio-Rad, USA) and normalized to protein content using the bicinchoninic acid (BCA) protein assay (Bio-Rad, USA). The GFP-positive cells were counted using a flow cytometer (EPICS ELITE ESP, COULTER, USA).

11. In Vivo Transfection Experiments

11.1 Complex Preparation

P(MDS-co-CES)/DNA complexes were prepared by gently mixing 10 μl of P(MDS-co-CES) solution (1.35 mg/mL) with 1.0 μl of GFP-plasmid encoding the GFPmut1 variant (PEGFP-C1) with 4.7 kb driven by the SV 40 early promoter (2.5 μg; Clontech, USA) in the sodium acetate/acetic acid (0.02 M, pH 4.6). The solutions were allowed to stand for 30 min before use.

11.2 Animal Surgery and Delivery of the Transgene Complexes

Albino guinea pigs weighing between 250 and 300 g were used for the study. The animals were initially anesthetized with a combination of ketamine (40 mg/kg) and the analgesic xylazine (10 mg/kg). The routine post-auricular approach was used to expose the tympanic bony bulla. A small opening was carefully made in the tympanic bulla with a pair of forceps to allow direct visualization of the round window membrane (RWM). A small piece of dry Gelfoam was placed in the groove, in direct contact with the RWM. An 11.0 μl of complex solution or naked DNA was injected into Gelfoan. Injection of the complexes or naked DNA into the Gelfoam prevents the spread of the solution to neighboring tissues. The incision was closed in layers, and the total operating time was approximately 20 minutes.

11.3 Tissue Processing

Animals implanted with Gelfoam containing DNA complexes or naked DNA were sacrificed at day 2, 4, 7 and 14 respectively post surgery. From these, the temporal bond was removed from both sides of the head. Each bulla was opened using rongeurs to expose the cochlea. The stapes was removed and the cochlea was fixed by the injection of 4% paraformaldehyde through the round window. The cochlea was then immersed in 4% paraformaldehyde overnight at 4° C. After complete fixation, specimens were decalcified in 10% EDTA for 5 days. After decalcification, the specimens were washed in PBS and dehydrated by immersion in increasing concentrations of alcohol, before being equilibrated in xylene. The specimens were then embedded in paraffin wax and sectioned radially at a thickness of 7 μm on a Leica microtome (RM2125RT).

11.4 Fluorescence Microscopy

Prior to microscopy, the tissue sections were dewaxed with xylene and mounted with Sigma mounting medium. The samples were then viewed under a confocal microscope (Olympus, Japan). Images were captured through a digital camera.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

In the claims (as well as in the specification above), all transitional phrases such as "comprising", "including", "carrying", "having", "containing", "involving", and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, section 2111.03.

What is claimed is:

1. An article for delivering a drug and a nucleic acid, the article comprising:
    a nanoparticle micelle, wherein the nanoparticle comprises a polymer having a polyester backbone comprising N-methyldietheneamine sebacate and [(cholesteryl oxocarbonylamido ethyl) methyl bis (ethylene) ammonium bromide] sebacate;
    a nucleic acid associated with an exterior of the micelle; and
    a drug associated with an interior of the micelle.

2. The article of claim 1, wherein the nanoparticle is capable of passing through a cell membrane.

3. The article of claim 1, wherein the nucleic acid is DNA.

4. The article of claim 1, wherein the drug is a cancer drug.

5. The article of claim 1, wherein the nanoparticle is stable at a concentration of greater than 5 mg/L.

6. The article of claim 1, wherein the nanoparticle is capable of crossing the blood/brain barrier.

7. A composition comprising the article of claim 1 and a pharmaceutically acceptable carrier.

8. The article of claim 1, wherein the polyester backbone comprises tertiary amines.

9. The article of claim 8, wherein the polyester backbone comprises a copolymer of quaternized and non-quaternized tertiary ammonium groups.

10. The article of claim 1, wherein the polyester backbone further comprises an ether linkage.

11. The article of claim 8, wherein at least a portion of the tertiary amines are quaternized and bound to a hydrophobic side chain.

12. The article of claim 1, wherein the polyester backbone further comprises a polyether.

13. A kit comprising:
    a container including an amphoteric polymeric nanoparticle micelle, wherein the polymeric nanoparticle comprises a polymer having a polyester backbone comprising N-methyldietheneamine sebacate and [(cholesteryl oxocarbonylamido ethyl) methyl bis (ethylene) ammonium bromide] sebacate;
    a nucleic acid associated with an exterior of the micelle;
    a drug associated with an interior of the micelle; and
    instructions for administering the nanoparticle to a subject.

14. The kit of claim 13, wherein the polyester backbone comprises a graft co-polymer.

15. The article of claim 1, wherein the polyester backbone comprises an amphiphilic co-polymer.

16. The article of claim 15, wherein the amphiphilic co-polymer is a cationic amphiphilic co-polymer.

17. The article of claim 1, wherein the drug is not covalently or ionically bound to the nanoparticle.

18. The article of claim 1, wherein the drug is physically contained by the nanoparticle.

19. The article of claim 1, wherein the polyester backbone comprises a graft co-polymer.

20. The article of claim 11, wherein the hydrophobic side chain comprises cholesterol.

* * * * *